United States Patent [19]

Shida et al.

[11] Patent Number: 4,863,935

[45] Date of Patent: Sep. 5, 1989

[54] MITOMYCIN COMPOUNDS HAVING USEFUL ANTI-TUMOR ACTIVITY

[75] Inventors: Yasushi Shida; Tokuyuki Kuroda, both of Shizuoka; Ikuo Matsukuma, Tokyo; Makoto Morimoto; Tadashi Ashizawa, both of Shizuoka, all of Japan

[73] Assignee: Kyowa Hakko Kogyo K.K., Japan

[21] Appl. No.: 131,619

[22] Filed: Dec. 11, 1987

[30] Foreign Application Priority Data

Dec. 13, 1986 [JP] Japan .................................. 61-296990

[51] Int. Cl.⁴ ............................................ C07D 487/14
[52] U.S. Cl. ...................... 514/322; 514/212; 514/231.5; 514/410; 546/199; 540/602; 544/69; 544/142; 548/406; 548/422
[58] Field of Search ................ 548/406, 422; 546/199; 540/602; 544/69, 142; 514/410, 212, 322, 227, 231.5

[56] References Cited

U.S. PATENT DOCUMENTS

| 4,268,676 | 5/1981 | Remers | 548/422 |
| 4,374,774 | 2/1983 | Kasai et al. | 548/422 |
| 4,691,024 | 9/1987 | Shirahata et al. | 548/422 |

FOREIGN PATENT DOCUMENTS

| 0116208 | 8/1984 | European Pat. Off. | 548/422 |
| 0163550 | 5/1985 | European Pat. Off. | 548/406 |
| 0197799 | 4/1986 | European Pat. Off. | 548/406 |
| 3413489 | 10/1984 | Fed. Rep. of Germany | 548/422 |
| 104386 | 6/1984 | Japan | 548/422 |
| 175493 | 10/1984 | Japan | 548/422 |
| 2121796 | 1/1984 | United Kingdom | 548/422 |
| 2134514 | 8/1984 | United Kingdom | 548/422 |

OTHER PUBLICATIONS

Shirahata, *JACS*, vol. 105, 1983, pp. 7199–7200.

*Primary Examiner*—Mary Lee
*Assistant Examiner*—Zinna Northington
*Attorney, Agent, or Firm*—Wolder, Gross & Yavner

[57] ABSTRACT

Mitomycin derivatives having potent anti-tumor activity against solid sarcoma 180 tumors and lymphocytic leukemia P-388 tumors.

9 Claims, No Drawings

MITOMYCIN COMPOUNDS HAVING USEFUL ANTI-TUMOR ACTIVITY

The present invention relates to new mitomycin derivatives having excellent anti-tumour activities and which are of interest in the preparation of anti-tumour compositions.

It is known that mitomycins have, in general, excellent anti-tumour activities. Examples of these mitomycins include mitomycin A, mitomycin B, mitomycin C, and porfiromycin, which are disclosed in the Merck Index, 10th Edition, mitomycin D and mitomycin E, which are disclosed in JP-A-122797/79, mitomycin F which is disclosed in JP-A-45322/80 and the like.

The amended chemical structures of these mitomycins are disclosed in J. Am. Chem. Soc., 105, 7199 (1983) and are shown in the following Table 1. These mitomycins may be prepared by culturing a microorganism of the species *Streptomyces caespitosus*.

TABLE 1

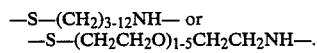

| | $X_A$ | $R_A$ | $R_B$ | 9 | 10 |
|---|---|---|---|---|---|
| Mitomycin A | $OCH_3$ | $CH_3$ | H | | |
| B | $OCH_3$ | H | $CH_3$ | | |
| C | $NH_2$ | $CH_3$ | H | ◄ | |
| D | $NH_2$ | H | $CH_3$ | | |
| E | $NH_2$ | $CH_3$ | $CH_3$ | | |
| F | $OCH_3$ | $CH_3$ | $CH_3$ | | |
| Porfiromycin | $NH_2$ | $CH_3$ | $CH_3$ | ◄ | |

Among them, mitomycin C is widely used for clinical purposes in view of its strong anti-tumour activity. However, various proposals have been put forward to provide improved mitomycin derivatives with enhanced anti-tumour activity and/or decreased undesirable side-effects since mitomycin C exhibits strong toxicity to bone marrow.

The known mitomycin derivatives include, for example, those having a substituted 7-amino group. The derivatives carrying sulphur at the substituted 7-amino group are exemplified by those carrying thiazolylamino, 2-thienylmethylamino and (4-sulfonamidophenyl)-methylamino (disclosed in JP-A-92288/81), 2-mercaptoethylamino, 2-ethylthioethylamino, thiomorpholino, thiazolidinyl, 4-mercaptoanilino, 2-(4-methylthiazolyl)amino, 2-(5-methyl-1,3,4-thiadiazolyl)amino and 4-(2,1,3-benzothiadiazolyl)amino (disclosed in JP-A-188590/82). Mitomycin derivatives are also known carrying at the 7th position a group of the formula:

—NHCH₂CH₂SSCH₂CH₂NH— exemplified by 7-N, 7'-N'-dithiodiethylenedimitomycin C, 7-N, 7'-N'-dithioethylenedimitomycin D, etc. (disclosed in EP-A-0116208 and JP-A-104386/84), those carrying at the 7th position a group of the formula:

RSS(CH₂)₂NH— exemplified by those in which R represents an alkyl or a substituted alkyl group such as, for example, 7-N-propyldithioethylmitomycin C, 7-N-methoxycarbonylmethyldithioethylmitomycin C and 7-N-[2-(2-hydroxyethyldithio)ethyl]mitomycin D (disclosed in EP-A-0116208 and JP-A-175493/84), those wherein R represents an aromatic ring having a substituent, exemplified by 7-N-[2-(4-acetoamidophenyldithio)ethyl]mitomycin C (disclosed in EP-A-0116208 and JP-A-175493/84), 7-N-[2-(4-fluorophenyldithio)ethyl]mitomycin C (disclosed in EP-A-0163550 and JP-A-255789/85) and those wherein R represents either an amino acid residue carrying a thiol or a peptide carrying a residual group of said amino acid such as 7-N-[2-[(L-cystein-S-yl)thio]ethyl]mitomycin D, 7-N-[2-[(glycino-L-cystein-S-yl)thio]ethyl]mitomycin D, etc. (disclosed in EP-A-0163550 and JP-A-255789/85).

JP-A-205382/84 discloses derivatives of mitomycin C carrying R-SS-alk₂ such as RSS(CH₂)₂NH— at the 7th position, of which R are partly the same as R disclosed in said JP-A-175493/84.

JP-A-1197/85 discloses mitomycin derivatives carrying at the 7th position a phenylamino group which is substituted at the p-position by a glycosylthio or glycosyloxy group of a 5–6 membered monosaccharide.

JP-A-194085/86 discloses dimers comprising 2 mitomycin skeletons linked together at the 7,7'-positions with —S—(CH₂)₃₋₁₂NH— or
—S—(CH₂CH₂O)₁₋₅CH₂CH₂NH—.

Mitomycin derivates are also known which carry as a substituent at the 7th position an acylthiopolymethyleneamino or thioacylthiopolymethyleneamino group (disclosed in EP-A-0197799), those carrying as a substituent at the 7th position

X'—SS—(CH₂)₃₋₈NH— wherein X' is an S-yl group of alkyl, cycloalkyl, pyridyl, unsubstituted or substituted phenyl, sulphur-containing amino acids, etc. (disclosed in WO 86/04898) and those carrying sulphur in the substituent at the 7th position (disclosed in JP-A-196570/86, 199519/86 and 203230/86).

The present invention thus provides mitomycin derivatives having excellent anti-tumor activity and having the formula:

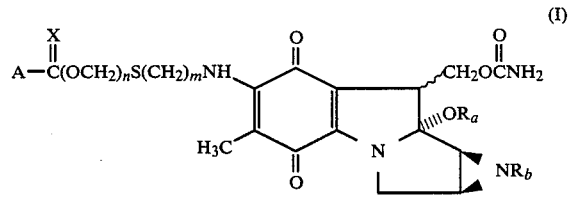

wherein

A is selected from the following (i) to (v):

wherein R₁ is selected from unsubstituted or substituted alkyl (wherein the substituent is one or more members independently selected from lower alkoxycarbonyl, benzyloxy, benzyloxycarbonyl, carboxy, halogen, hydroxy, lower alkoxy, lower alkanoyloxy, trilower alkylsilyloxy, amino, lower alkylamino, dilower alkylamino and benzyloxycarbonylamino), unsubstituted or substituted cycloalkyl (wherein the substituent is one or more members independently selected from lower alkyl, lower alkoxycarbonyl, benzyloxycarbonyl, carboxy, halogen, hydroxy, lower alkoxy, lower alkanoyloxy, trilower alkylsilyloxy, amino, lower alkylamino, dilower alkylamino and benzyloxycarbonylamino), unsubstituted or substituted aralkyl (wherein the benzene nucleus is substituted by one or more members independently selected from lower alkoxy, halogen, lower alkyl, nitro, hydroxy, amino, cyano and carboxy), 2-benzyloxycarbonyl-1-phenylethyl and

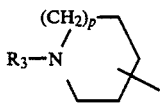

(wherein R₃ is selected from hydrogen, benzyl, lower alkyl, lower alkanoyl and benzyloxycarbonyl; and p is 0 or 1) and R₂ represents hydrogen; or R₁ and R₂ each independently represents alkyl;
(ii) morpholino;

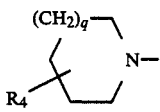 (iii)

wherein R₄ is selected from hydrogen, hydroxy, lower alkoxy, lower alkanoyloxy, lower alkylamino, dilower alkylamino, benzyloxycarbonylamino and benzyl; and q is 0 or 1;

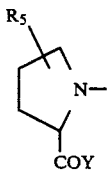 (iv)

wherein R₅ represents hydrogen or hydroxy; Y represents hydroxy, lower alkoxy, benzyloxy, lower alkanoyloxymethoxy, amino, lower alkylamino, dilower alkylamino, benzylamino or

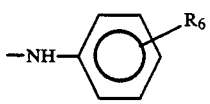

(wherein R₆ represents hydrogen or hydroxy); and

 (v)

wherein R₇ is selected from hydrogen, lower alkanoyl, trifluoroacetyl, benzoyl, benzyloxycarbonyl, lower alkoxycarbonyl, lower alkyl and benzyl; and R₈ represents hydrogen or lower alkyl;

n is 0 or 1, provided that when n is 0, X represents oxygen or sulphur and when n is 1, X is oxygen;

m is an integer of from 2 to 8; and

R$_a$ and R$_b$ each independently represents hydrogen or methyl provided that R$_a$ and R$_b$ do not both represent hydrogen.

Hereinafter, compounds of the formula (I) are referred to as Compounds (I). Compounds represented by other formulae are referred to similarly.

Where Compounds (I) are carboxylic acids, their salts also exhibit excellent anti-tumour activity, which are exemplified by various salts formed with alkali metals (e.g. sodium and potassium) and alkaline earth metals (e.g. calcium and magnesium) and ammonium salts.

With regard to the definition of R₁ and R₂ in formula (I), alkyl groups which may be unsubstituted or substituted include straight or branched alkyl carrying 1–18 carbon atoms and preferably exemplified by methyl, ethyl, propyl, isopropyl, n-butyl, isobutyl, sec-butyl, tert-butyl, n-pentyl, isopentyl, tertpentyl, neopentyl, n-hexyl, isohexyl, 3-methylpentyl, 2-methylpentyl, 1-methylpentyl, 1,3-dimethylbutyl, 3,3-dimethylbutyl, 2-ethylbutyl, 2,4-dimethyl-3-pentyl, 2,2-dimethyl-3-pentyl, 2,2-dimethyl-3-pentyl, n-octyl, 2-ethylhexyl, 2,2,4,4-tetramethyl-3-pentyl n-decyl and n-octadecyl.

Usually, the alkyl group may carry one or two substituents which may be the same or different. With regard to the preferred substituents, lower alkoxycarbonyl include straight or branched alkoxycarbonyl carrying 2–5 carbon atoms and exemplified by methoxycarbonyl, ethoxycarbonyl, n-propoxycarbonyl and tert-butoxycarbonyl. Preferred halogens include, for example, fluorine, chlorine and bromine. Lower alkoxy include straight or branched alkoxy carrying 1–4 carbon atoms such as, for example, methoxy, ethoxy, n-propoxy, n-butoxy and tert-butoxy. Lower alkanoyloxy are exemplified by alkanoyloxy carrying 1–5 carbon atoms, for example, formyloxy, acetyloxy, propionyloxy, n-butyryloxy and pivaloyloxy. Trilower alkylsilyloxy include, for example, trialkylsilyloxy (which contain alkyl groups having 1–4 carbon atoms which may be the same or different) which are exemplified by trimethysilyloxy, triethylsilyloxy and tertbutyldimethylsilyloxy. Lower alkylamino includes straight or branched alkylamino carrying 1–4 carbon atoms and exemplified by methylamino, ethylamino, n-propylamino, isopropylamino and n-butylamino.

Examples of dilower alkylamino include dialkylamino containing two straight or branched alkyl carrying 1–4 carbon atoms, which may be the same or different e.g. dimethylamino, diethylamino and di-n-butylamino.

With regard to the definition of R₁ and R₂ in the formula (I), unsubstituted or substituted cycloalkyl include those carrying 3–6 carbon atoms, which are exemplified by cyclopropyl, cyclobutyl, cyclopentyl and cyclohexyl. The cycloalkyl group usually contains one or two substituents which may be the same or different. With regard to the substituents of cycloalkyl, lower alkyl include straight or branched alkyl carrying 1–4 carbon atoms, for example, methyl, ethyl, n-propyl, isopropyl and n-butyl. The definitions of lower alkoxycarbonyl, halogen, lower alkoxy, lower alkanoyloxy, trilower alkylsilyloxy, lower alkylamino and dilower alkylamino are the same as mentioned in the definition of the substituted alkyl hereinbefore.

With regard to the definition of $R_1$ and $R_2$ in the formula (I), unsubstituted or substituted aralkyl include benzyl, phenethyl and diphenylmethyl, which usually contain one or two substituents which may be the same or different. Among such substituents, lower alkoxy include straight or branched alkoxy carrying 1–4 carbon atoms, for example, methoxy and ethoxy. Halogens are exemplified by fluorine and chlorine. Lower alkyl include straight and branched alkyl carrying 1–4 carbon atoms, for example, methyl, ethyl and isopropyl.

With regard to the definition of $R_3$ in the formula (I), lower alkyl include straight or branched alkyl carring 1–4 carbon atoms, for example, methyl, ethyl, n-propyl, isopropyl and n-butyl. Lower alkanoyl includes straight or branched alkanoyl carrying 1–4 carbon atoms, for example, formyl, acetyl, propionyl and n-butyryl.

In the formula (I) where $R_1$ and $R_2$ each independently represents alkyl such alkyl has the same meaning as that hereinbefore described for unsubstituted or substituted alkyl in the definition of $R_1$ and $R_2$.

With regard to the definition of $R_4$ in the formula (I), lower alkoxy includes straight or branched alkoxy carrying 1–4 carbon atoms, for example, methoxy, ethoxy, isopropoxy and n-butoxy, and lower alkanoyloxy includes straight or branched alkanoyloxy carrying 1–4 carbon atoms, for example, formyloxy, acetyloxy, proionyloxy and n-butyryloxy. Lower alkylamino includes straight or branched alkylamino carrying 1–4 carbon atoms, for example, methylamino, ethylamino, n-propylamino, isopropylamino and n-butylamino. Dilower alkylamino includes straight or branched dialkylamino carrying 1–4 carbon atoms, which may be the same or different, and are exemplified by dimethylamino and diethylamino.

With regard to the definition of Y in the formula (I), lower alkoxy includes straight or branched alkoxy carrying 1–6 carbon atoms, for example, methoxy, ethoxy, n-propoxy, isopropoxy, n-butoxy, n-pentoxy and n-hexyloxy. Lower alkanoyloxymethoxy includes straight or branched alkanoyloxymethoxy carrying 2–5 carbon atoms, for example, formyloxymethoxy, acetyloxymethoxy, propionyloxymethoxy, and n-butyryloxymethoxy. Lower alkylamino includes straight or branched alkylamino, for example, methylamino, ethylamino, n-propylamino and n-butylamino. Dilower alkylamino includes alkylamino containing two straight or branched alkyl groups carrying 1–4 carbon atoms, which may be the same or different, and are exemplified by dimethylamino and diethylamino.

With regard to the definition of $R_7$ in the formula (I), lower alkanoyl includes straight or branched alkanoyl carrying 1–4 carbon atoms, for example, formyl, acetyl, propionyl, n-butyryl and isobutyryl. Lower alkoxycarbonyl includes, for example, straight or branched alkoxycarbonyl carrying 2–5 carbon atoms, for example, methoxycarbonyl and ethoxycarbonyl. Lower alkyl includes straight or branched alkyl carrying 1–4 carbon atoms, for example, methyl, ethyl and n-propyl.

With regard to the definition of $R_8$ in the formula (I), the term lower alkyl has the same meaning as that used in the definition of $R_7$.

Compounds (I) may be obtained by the following process steps:

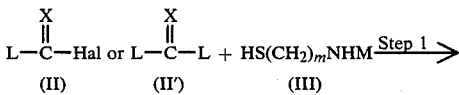
(II)    (II')    (III)

-continued

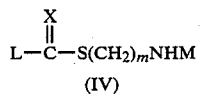
(IV)

(IV) + AH or an acid addition salt thereof $\xrightarrow{\text{Step 2}}$
(V)

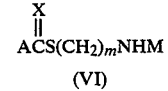
(VI)

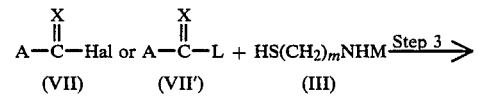
(VII)    (VII')    (III)

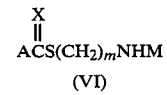
(VI)

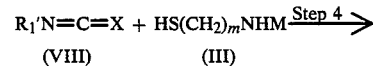
(VIII)    (III)

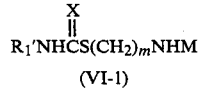
(VI-1)

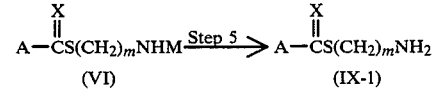
(VI)        (IX-1)

AH of an acid addition salt thereof + HalCOCH$_2$Hal $\xrightarrow{\text{Step 6}}$
(V)            (X)

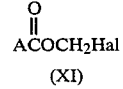
(XI)

(XI) + HS(CH$_2$)$_m$NHM $\xrightarrow{\text{Step 7}}$ ACOCH$_2$S(CH$_2$)$_m$NHM
(III)                 (XII)

(XII) $\xrightarrow{\text{Step 8}}$ A—COCH$_2$S(CH$_2$)$_m$NH$_2$
                      (IX-2)

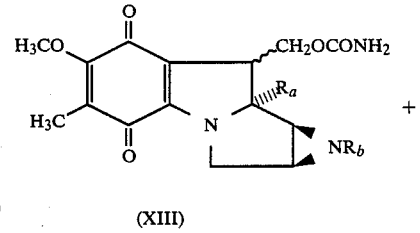
(XIII)

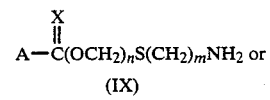
(IX)

an acid addition salt thereof $\xrightarrow{\text{Step 9}}$

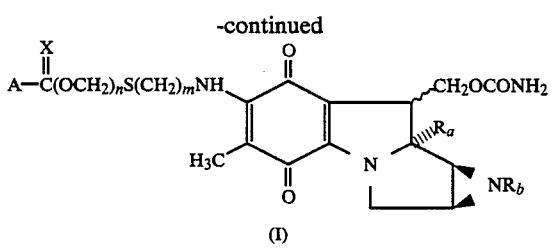

(In the above-mentioned steps, X, m, A, n, $R_a$ and $R_b$ are the same as those defined in the formula (I) hereinbefore; $R_1'$ has the same meaning as $R_1$ defined in the formula (I) in the case where $R_2$ is hydrogen; L represents a leaving group; Hal is a halogen; and M is a group used for the protection of the amino group.)

In the above-mentioned formulae, preferred examples of the leaving group L include p-nitrophenyloxy, chloromethyloxy and imidazolyl. Although any and all groups used conventionally for the protection of amino groups may be used as M, it is preferred to use those, of which protection may be removed by acids, for example, benzyloxycarbonyl, p-methoxybenzyloxycarbonyl, tert-butyloxycarbonyl, di-(p-methoxyphenyl)methyl and triphenylmethyl.

Preferred acid addition salts of Compound (V) include, for example, inorganic acid salts such as hydrochloride, hydrobromate or sulfate; and organic acid salts such as formate, acetate, p-toluenesulfonate or trifluoroacetate.

Step 1

Compound (IV) may be produced by the reaction of Compound (II) or (II') with Compound (III) in an inert solvent, preferably in the presence of a base. It is preferred to use 1.0–1.2 moles of Compound (II) or (II') per mole of Compound (III). Preferred inert solvents include, for example, chloroform, dichloromethane, tetrahydrofuran, acetonitrile, dimethyl sulfoxide and dimethylformamide, any of which may be used alone or in admixture under anhydrous conditions.

Preferred bases are exemplified by inorganic bases such as sodium carbonate, potassium carbonate, sodium bicarbonate, sodium hydroxide, potassium hydroxide and lithium hydroxide; tertiary amines such as pyridine; 4-dimethylaminopyridine, triethylamine, and N,N-dimethylaniline; and alkali metal alkoxides such as sodium methoxide, sodium ethoxide, potassium methoxide, and potassium ethoxide, of which 1.0–3.0 moles may usually be used per mole of Compound (II) or (II').

The reaction may be effected at a temperature of from 0° to 70° C. The reaction time is usually 0.5 to 18 hours.

Step 2

Compound (VI) which is a derivative of thiocarbamate or dithiocarbamate is obtained by the reaction or Compound (IV) which is either a reactive derivative of carboxylic acid or a reactive derivative of thiocarboxylic acid, with Compound (V) which is an amine or an acid addition salt thereof in an inert solvent, if desired, in the presence of a base.

Preferred inert solvents include, for example, acetonitrile, dimethylformamide, dimethyl sulfoxide, tetrahydrofuran, dichloromethane and chloroform, any of which may be used alone or in admixture. The bases which may be used in Step 1 may also be used in this step. The use of a base is required when an acid addition salt of Compound (V) is used. Where Compound (V) is used in the free form, the use of a base is preferred. It is possible to use 1.0–5.0 moles of Compound (V) or an acid addition salt thereof per mole of Compound (IV). When an acid addition salt of Compound (V) is used, an additional amount of the base is required to neutralize the acid.

It is preferred to carry out the reaction at a temperature of from 0° to 70° C. Usually the reaction is continued for a period of 0.5 to 18 hours.

Step 3

Compound (VI) may also be produced by the reaction of Compound (VII) or (VII') with Compound (III) in an inert solvent.

It is preferred to use 1.0–5.0 moles of Compound (III) per mole of Compound (VII) or (VII'). In some cases, it is preferred to carry out the reaction in the presence of a base. For this purpose, the bases used in Step 1 may be used, for example, 1.0–5.0 moles of base per mole of Compound (III).

The inert solvents used in Step 2 may be used in this step alone or in admixture under anhydrous conditions. The reaction may be effected at a temperature of from 0° to 70° C. Usually the reaction is continued for a period of 0.5 to 18 hours.

Step 4

Compound (VI-l), a sub-class of Compound (VI), may be produced by the reaction of Compound (VIII) which is either an isocyanate or isothiocyanate, with Compound (III) which is a thiol compound, in an inert solvent.

It is preferred to use 1.0–5.0 moles of Compound (VIII) per mole of Compound (III). The inert solvents which may be used in the foregoing steps may also be used in this step, alone or in admixture, under anhydrous conditions. The reaction may be effected at a temperature of from 0° to 70° C., and usually may be continued for a period of 0.5 to 18 hours.

Step 5

The protecting group of Compound (VI) which was prepared in Steps 1 and 2, 3 or 4 is removed in this step, wherein Compound (IX-l) is prepared by the reaction of Compound (VI) with a compound which is suitable for removing the protecting group in an inert solvent. If desired, it is also possible to use such a compound itself as a solvent.

Preferred compounds for such a purpose include, for example, formic acid, acetic acid, hydrobromic acid-acetic acid, trifluoroacetic acid, hydrogen chloride and p-toluenesulfonic acid, of which 1.0–10 moles per mole of Compound (VI) may usually be used.

It is also possible to use a greater amount of such a compound, if it is used as a solvent at the same time. Preferred inert solvents include, for example, water, chloroform, dichloromethane, acetonitrile, tetrahydrofuran and lower alkanols (for example, methanol, ethanol and ispropanol). The reaction may be effected at a temperature of from 0° to 70° C. and usually continued for a period of from 0.5 to 18 hours.

Step 6

Compound (XI) may be obtained by the reaction of Compound (V) or an acid addition salt thereof with Compound (X) in an inert solvent, if desired, in the presence of a base. 1.0-1.2 moles of Compound (V) may be used per mole of Compound (X). The inert solvents which may be used in Step 1 may also be used in this step alone or in admixture under anhydrous conditions. When an acid addition salt of Compound (V) is used, an additional amount of the base may be required to liberate Compound (V).

For this purpose, the bases which may be used in Step 1 may also be used. In some cases where Compound (V) is used in the free form, better results may be obtained by using a base. In such a case, the use of 1.0-5.0 moles of the base per mole of Compound (X) may be preferred.

The reaction may be effected at a temperature of from 0° to 70° C. Usually the reaction may be continued for a period of from 1 to 18 hours.

Step 7

Compound (XII) is obtained by the reaction of Compound (XI) with Compound (III) in an inert solvent in the presence of a base.

Preferred inert solvents, which include those used in Step 2 and acetone may be used alone or in admixture under anhydrous conditions. Although various bases which may be used in Step 2 may also be used in this step for trapping hydrogen halide it is preferred to use, for example, silver carbonate and silver oxide. Especially good results may be obtained by the use of silver carbonate or silver oxide, particularly in the presence of sodium iodide or potassium iodide. In such a case, it is preferred to use 1.0-5.0 moles of sodium iodide or potassium iodide per mole of silver carbonate or silver oxide. The use of 1.0-5.0 moles of sodium iodide or potassium iodide per mole of Compound (XI) is preferred. It is also possible to use 1.0-1.2 moles of Compound (III) per mole of Compound (XI).

The reaction may be effected at a temperature of from 0° to 70° C. Usually the reaction may be continued for a period of from 0.5 to 18 hours.

Step 8

The group used for the protection of the amino group of Compound (XII) is removed in a similar manner to that described in Step 5.

Step 9

Compound (I) is prepared by the reaction of Compound (XIII), a derivative of mitomycin having a methoxy group at the 7th position, with Compound (IX) or its acid addition salt in an inert solvent, if desired, in the presence of a base. The acid addition salt of Compound (IX) may be prepared by the reaction of this compound with a salt in conventional manner used for the formation of various salts. It is preferred to use 1-10 moles of Compound (IX) or its acid addition salt per mole of Compound (XIII). In the case where an acid addition salt of Compound (IX) is used, an additional amount of the base is required to liberate Compound (IX). In this step, it is possible to use the bases which may be used in Step 2. In some cases where Compound (XIII) and a free Compound (IX) are used for the reaction, better results may be given by the use of a base.

Preferred inert solvents include, for example, methanol, ethanol, isopropanol, and other lower alkanols; acetonitrile, dimethylformamide, dimethyl sulfoxide and tetrahydrofuran, any of which may be used alone or in admixture.

It is preferred to carry out the reaction at a temperature of from 0° C. to ambient temperature, and the reaction is usually continued for a period of from 30 minutes to 18 hours.

In the above-mentioned steps, the reaction products may be isolated and purified in conventional manner used for isolation and purification of products obtained by synthesis for example, extraction, chromatographic treatment and recrystallization.

Compounds (I) may be used for the preparation of anti-tumour agents with respect to their excellent anti-tumour activity and decreased toxicity against bone marrow. Especially good results may be obtained from the compounds of formula (I) wherein X is oxygen or sulphur;
n is 0;
m is an integer of from 2 to 8 (particularly 2);
$R_a$ is methyl;
$R_b$ is hydrogen;
9〰〰10 represents ▬ ; and
A is selected from the following (i)–(iv):

(i)

wherein $R_1$ is selected from unsubstituted alkyl, benzyloxysubstituted alkyl, unsubstituted aralkyl (particularly benzyl), and

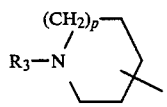

(wherein $R_3$ is benzyl; p is 0 or 1) and $R_2$ represents hydrogen;

(ii) morpholino;

(iii)

wherein $R_4$ represents hydrogen, hydroxy and benzyl, and q is 0 or 1; and

(iv)

wherein $R_5$ represents hydrogen or hydroxy, and Y is selected from lower alkoxy, amino, lower alkylamino, dilower alkylamino, and benzylamino.

With regard to the so-called chemotherapeutic index viz. the CI value against sarcoma 180 solid tumour, expressed by the formula:

$$CI = (LD_{50})/(ED_{50})$$

and the CI value against bone marrow toxicity, expressed by the formula:

$CI = (WBC_{4000})/(ED_{50})$.

In general, one of the two CI values of each of the compounds of formula (I) described herein is superior to the corresponding value of mitomycin C, while the other value is equal or superior to the corresponding value of mitomycin C.

Also, their therapeutic indexes, expressed by the formula:

$$TI = (OPD)/(\text{dose which results in ILS}_{30}),$$

against lymphocytic Leukemia P-388 and the maximum increased life spans ($ILS_{max}$), defined by the formula:

$$ILS = (T-C)/C \times 100,$$

are superior to the corresponding values of mitomycin C. For clinical purposes, the increased CI values of the compounds of the present invention provide broader tolerances for the drug dose, which is advantageous for more effective anti-tumour therapy with decreased toxicity. The provision of mitomycin derivatives with higher CI values is thus a technical advance in the art.

As used herein, the term "$LD_{50}$" denotes the acute toxicity. The term "$ED_{50}$" denotes the administered amount needed for reducing the volume of Sarcoma 180 solid tumours in animals to 50% of the corresponding tumour volume in control (untreated) animals. The term "$WBC_{4000}$" denotes the minimum dose of the drug needed to reduce the number of peripheral leucocytes to $4000/mm^3$. A greater TI value results in a broader tolerance to the drug, which is advantageous for higher anti-tumour activity and decreased toxicity. The term "T" used herein denotes the average survival days of the test animals administered with the test compound. The term "C" denotes the average survival days of the control (untreated) animals. The term "OPD" denotes the dose of the drug resulting in the highest survival ratio. The term "$ILS_{30}$" denotes a 30% increase of life-span.

Compounds (I) may be used for the preparation of anti-tumour pharmaceutical compositions comprising an effective amount of a Compound (I) in association with at least one pharmaceutically acceptable carrier and/or adjuvant. Thus, such compositions may contain, for example, various diluents, excipients, disintegrating agents, binders, lubricants and formulation fillers conventionally used in the pharmaceutical art.

Compounds (I) may be administered in various forms. For the preparation of injection agents, for example, Compound (I) is dissolved in a suitable diluent used conventionally in the art (e.g. ethanol), which may if desired contain, for example, a surfactant and/or solubilizing agent. The solution, with or without removal of ethanol is mixed, for example, with sterilized water suitable for injection, which may if desired contain, for example, glucose, fructose, and/or mannitol. If desired, injection agent may be prepared by freeze-drying the ethanol solution. It is also possible to prepared injection powders by mixing Compound (I) with sodium chloride. For use, these preparations may be suitably dissolved.

Although the injection agents are usually injected intravenously, it is also possible to administer the composition, for example, by injection into the muscle, artery, abdominal cavity or thoracic cavity.

Compositions for administration by oral route may be prepared by mixing Compound (I) with suitable excipients, disintegrating agents, binders, lubricants and the like and formulating the mixture into, for example, tablets, granules or powders in conventional manner. It is also possible to prepare suppositories by mixing Compound (I) with suitable excipients, followed by conventional formulation.

Although the optimum dose may vary depending for example, upon the administration schedule, the particular Compound (I), the ages and symptoms of the patients and the like, one may, for example, administer Compounds (I) to mammals, including humans, at a daily dosage in the range of 0.5–75 mg/60 kg.

Selected Compounds (I) and their structures are shown in the following Tables 2 and 3 respectively. In these tables, the compounds are numbered by referring to the corresponding Examples hereinafter described.

TABLE 2

| No. | Compound name |
|---|---|
| 1 | 7-N—(2-methylaminocarbonylthioethyl)mitomycin C |
| 2 | 7-N—[2-(2-t- butoxycarbonylethyl)aminocarbonyloxy-methylthioethyl]mitomycin C |
| 3 | 7-N—[2-(2-benzyloxycarbonylethyl)aminocarbonyl-thioethyl]mitomycin C |
| 4 | 7-N—(2-diethylaminocarbonylthioethyl)mitomycin C |
| 5 | 7-N—(2-t-butylaminocarbonylthioethyl)mitomicin C |
| 6 | 7-N—[2-((S)—2-methoxycarbonylpyrrolidino)carbonylthioethyl]mitomycin C |
| 7 | 7-N—(2-isopropylaminocarbonylthioethyl)mitomycin C |
| 8 | 7-N—(2-dimethylaminocarbonylthioethyl)mitomycin C |
| 9 | 7-N—[2-((S)—1-methoxycarbonyl-2-methylpropyl)-aminocarbonylthioethyl]mitomycin C |
| 10 | 7-N—[2-(1-phenyl-2-benzyloxycarbonylethyl)amino-carbonylthioethyl]mitomycin C |
| 11 | 7-N—[2-(1-ethylpropyl)aminocarbonylthioethyl]-mitomycin C |
| 12 | 7-N—[2-(1-benzylpiperidine-4-yl)aminocarbonyl-thioethyl]mitomycin C |
| 13 | 7-N—[(2-(1-benzyloxymethyl-2-methylpropyl)amino-carbonylthioethyl]mitomycin C |
| 14 | 7-N—[2-((S)—2-benzylaminocarbonylpyrrolidino)-carbonylthioethyl]mitomycin C |
| 15 | 7-N—[2-((S)—2-t-butoxycarbonylpyrrolidino)-carbonylthioethyl]mitomycin C |
| 16 | 7-N—[2-((S)—2-benzyloxycarbonylpyrrolidino)-carbonylthioethyl]mitomycin C |
| 17 | 7-N—[2-((S)—2-methylaminocarbonylpyrrolidino)-carbonylthioethyl]mitomycin C |
| 18 | 7-N—[2-((S)—2-dimethylaminocarbonylpyrrolidino)carbonylthioethyl]mitomycin C |
| 19 | 7-N—[2-((S)—2-carbamoylpyrrolidino)carbonyl-thioethyl]mitomycin C |
| 20 | 7-N—[2-((S)—2-pivaloyloxymethyloxycarbonyl-pyrrolidino)-carbonylthioethyl]mitomycin C |
| 21 | 7-N—(2-pyrrolidinocarbonylthioethyl)mitomycin C |
| 22 | 7-N—(2-benzylaminocarbonylthioethyl)mitomycin C |
| 23 | 7-N—(2-ethylaminocarbonylthioethyl)mitomycin C |
| 24 | 7-N—(2-isobutylaminocarbonylthioethyl)mitomycin C |
| 25 | 7-N—(2-methylaminothiocarbonylthioethyl)mitomycin C |
| 26 | 7-N—(2-methylaminothiocarbonylthioethyl)mitomycin C |
| 27 | 7-N—(2-n-propylaminocarbonylthioethyl)mitomycin C |
| 28 | 7-N—(2-n-butylaminocarbonylthioethyl)mitomycin C |
| 29 | 7-N—(2-cyclohexylaminocarbonylthioethyl)mitomycin C |
| 30 | 7-N—(2-sec-butylaminocarbonylthioethyl)mitomycin C |
| 31 | 7-N—[2-((S)—2-carboxypyrrolidino)carbonylthioethyl]-mitomycin C (sodium salt) |
| 32 | 7-N—[2-((S)—2-methoxycarbonylpyrrolidino)carbonyl-thioethyl]mitomycin C |
| 33 | 7-N—(2-morpholinocarbonylthioethyl)mitomycin C |
| 34 | 7-N—[2-(1-methyl-1-t-butoxycarbonylethyl)-aminocarbonylthioethyl]mitomycin C |
| 35 | 7-N—[2-(1-methyl-2-formylhydrazino)carbonylthio-ethyl]mitomycin C |
| 36 | 7-N—[2-(1-methyl-2-formylhydrazino)carbonylthio-ethyl]mitomycin D |
| 37 | 7-N—(2-cyclohexylaminothiocarbonylthioethyl)-mitomycin C |
| 38 | 7-N—(2-cyclohexylaminothiocarbonylthioethyl)-mitomycin D |

TABLE 2-continued

| No. | Compound name |
|-----|---------------|
| 39 | 7-N—(2-ethylaminothiocarbonylthioethyl)mitomycin C |
| 40 | 7-N—(2-n-propylaminothiocarbonylthioethyl)mitomycin C |
| 41 | 7-N—[2-(4-benzylpiperidino)carbonylthioethyl]-mitomycin C |
| 42 | 7-N—(2-piperidinocarbonylthioethyl)mitomycin C |
| 43 | 7-N—[2-(4-hydroxypiperidino)carbonylthioethyl]-mitomycin C |
| 44 | 7-N—[2-((S)—2-methoxycarbonyl-(SR)-4-hydroxy-pyrrolidino)carbonylthioethyl]mitomycin C |
| 45 | 7-N—{2-[(S)—2-(4-hydroxyanilino)carbonyl-piperidino]carbonylthioethyl}mitomycin C |
| 46 | 7-N—[2-(1-isopropyl-2-methylpropyl)aminocarbonyl-thioethyl]mitomycin C |
| 47 | 7-N—[2-(trans-2-cis-6-dimethyl-cyclohexyl)amino-carbonylthioethyl]mitomycin C |
| 48 | 7-N—[2-(1-hydroxymethyl-2-methylpropyl)amino-carbonylthioethyl]mitomycin C |
| 49 | 7-N—[2-{2-(2-pyridyl)ethyl}aminocarbonylthioethyl]-mitomycin C |
| 50 | 7-N—(2-diphenylmethylaminothiocarbonylethyl)-mitomycin C |

TABLE 3

| No. | A | X | m | n | $R_3$ | $R_b$ |
|-----|---|---|---|---|-------|-------|
| 1 | CH$_3$NH— | O | 2 | 0 | CH$_3$ | H |
| 2 | (CH$_3$)$_3$C—OCOCH$_2$CH$_2$NH— | O | 2 | 1 | CH$_3$ | H |
| 3 | C$_6$H$_5$—CH$_2$OCOCH$_2$CH$_2$NH— | O | 2 | 0 | CH$_3$ | H |
| 4 | (CH$_2$CH$_2$)$_2$N— | O | 2 | 0 | CH$_3$ | H |
| 5 | (CH$_3$)$_3$CNH— | O | 2 | 0 | CH$_3$ | H |
| 6 | 2-(methoxycarbonyl)pyrrolidin-1-yl (L form) | O | 2 | 0 | CH$_3$ | H |
| 7 | (CH$_3$)$_2$CHNH— | O | 2 | 0 | CH$_3$ | H |
| 8 | (CH$_3$)$_2$N— | O | 2 | 0 | CH$_3$ | H |
| 9 | (CH$_3$)$_2$CHCH(COOCH$_3$)NH— | O | 2 | 0 | CH$_3$ | H |
| 10 | C$_6$H$_5$CH$_2$OCOCH$_2$CH(C$_6$H$_5$)NH— | O | 2 | 0 | CH$_3$ | H |
| 11 | (CH$_3$CH$_2$)$_2$CHNH— | O | 2 | 0 | CH$_3$ | H |
| 12 | 1-benzyl-4-piperidylamino— | O | 2 | 0 | CH$_3$ | H |
| 13 | CH$_3$—CH(CH$_3$)CH(CH$_2$OCH$_2$C$_6$H$_5$)—NH— | O | 2 | 0 | CH$_3$ | H |
| 14 | 2-(N-benzylcarbamoyl)pyrrolidin-1-yl (L form) | O | 2 | 0 | CH$_3$ | H |

TABLE 3-continued

| No. | A | X | m | n | R₃ | R_b |
|---|---|---|---|---|---|---|
| 15 | pyrrolidine-N— with COOC(CH₃)₃ (L form) | O | 2 | 0 | CH₃ | H |
| 16 | pyrrolidine-N— with COOCH₂-phenyl (L form) | O | 2 | 0 | CH₃ | H |
| 17 | pyrrolidine-N— with CONHCH₃ (L form) | O | 2 | 0 | CH₃ | H |
| 18 | pyrrolidine-N— with CON(CH₃)₂ (L form) | O | 2 | 0 | CH₃ | H |
| 19 | pyrrolidine-N— with CONH₂ (L form) | O | 2 | 0 | CH₃ | H |
| 20 | pyrrolidine-N— with COOCH₂OC(=O)C(CH₃)₃ (L form) | O | 2 | 0 | CH₃ | H |
| 21 | pyrrolidine-N— | O | 2 | 0 | CH₃ | H |
| 22 | phenyl-CH₂NH— | O | 2 | 0 | CH₃ | H |
| 23 | CH₃CH₂NH— | O | 2 | 0 | CH₃ | H |
| 24 | CH₃CHCH₂NH— with CH₃ | O | 2 | 0 | CH₃ | H |
| 25 | CH₃NH— | S | 2 | 0 | CH₃ | H |
| 26 | CH₃NH— | S | 2 | 0 | H | CH₃ |
| 27 | CH₃CH₂CH₂NH— | O | 2 | 0 | CH₃ | H |
| 28 | CH₃CH₂CH₂CH₂NH— | O | 2 | 0 | CH₃ | H |
| 29 | cyclohexyl-NH— | O | 2 | 0 | CH₃ | H |

TABLE 3-continued

| No. | A | X | m | n | $R_3$ | $R_b$ |
|---|---|---|---|---|---|---|
| 30 | CH₃CH₂CH(CH₃)NH— | O | 2 | 0 | $CH_3$ | H |
| 31 | pyrrolidine-N— with COONa (L form) | O | 2 | 0 | $CH_3$ | H |
| 32 | pyrrolidine-N— with COOCH₃ (D form) | O | 2 | 0 | $CH_3$ | H |
| 33 | morpholine-N— | O | 2 | 0 | $CH_3$ | H |
| 34 | (CH₃)₃COC(=O)C(OCH₃)(CH₃)NH— | O | 2 | 0 | $CH_3$ | H |
| 35 | CHONH—N(CH₃)— | O | 2 | 0 | $CH_3$ | H |
| 36 | CHONH—N(CH₃)— | O | 2 | 0 | H | $CH_3$ |
| 37 | cyclohexyl-NH— | S | 2 | 0 | $CH_3$ | H |
| 38 | cyclohexyl-NH— | S | 2 | 0 | H | $CH_3$ |
| 39 | CH₃CH₂NH— | S | 2 | 0 | $CH_3$ | H |
| 40 | CH₃CH₂CH₂NH— | S | 2 | 0 | $CH_3$ | H |
| 41 | 4-benzylpiperidine-N— | O | 2 | 0 | $CH_3$ | H |
| 42 | piperidine-N— | O | 2 | 0 | $CH_3$ | H |
| 43 | 4-hydroxypiperidine-N— | O | 2 | 0 | $CH_3$ | H |
| 44 | 4-hydroxypyrrolidine-N— with COOCH₃ (L form) | O | 2 | 0 | $CH_3$ | H |

TABLE 3-continued

| No. | A | X | m | n | $R_3$ | $R_b$ |
|---|---|---|---|---|---|---|
| 45 | (pyrrolidinyl-CONH-C6H4-OH, L form) | O | 2 | 0 | $CH_2$ | H |
| 46 | $((CH_3)_2CH)_2CHNH-$ | O | 2 | 0 | $CH_3$ | H |
| 47 | (cyclohexyl-NH-) | O | 2 | 0 | $CH_3$ | H |
| 48 | $HO-C(CH_3)_2-NH-$ | O | 2 | 0 | $CH_3$ | H |
| 49 | (2-pyridyl-$CH_2CH_2NH-$) | O | 2 | 0 | $CH_3$ | H |
| 50 | (diphenyl-CHNH-) | S | 2 | 0 | $CH_3$ | H |

Our invention is illustrated in the following Examples and Experiments. The NMR spectra of the compounds described in the examples are shown in Table 4. Their data obtained by the mass spectrometry and IR are shown in Table 5. The NMR and IR spectra were respectively obtained by the FAB (Fast Atom Bombardment) method and the KBr tablet method.

EXAMPLE 1

2-methylaminocarbonylthioethylamine (crude formate) was prepared in a similar manner to that described in Reference 4. The product (187 mg) was dissolved in anhydrous methanol (3 ml). To the solution were added triethylamine (450 mg; 5 molar equivalents) and mitomycin A (289 mg: 0.8 molar equivalents). The reaction solution was stirred at room temperature for 4 hours and was then concentrated under reduced pressure. The residue was dissolved in chloroform (50 ml). The solution was washed well with water and a saturated solution of sodium chloride. The chloroform layer was concentrated under reduced pressure. The residue was purified by silica gel chromatography using a solvent system of chloroform/methanol (9:1 v/v) to obtain Compound 1 (103 mg) in the form of grayish blue powders with a yield of 28%.

EXAMPLE 2

2-(2-t-butoxycarbonylethyl)aminocarbonyloxymethylthioethylamine (acetate; 113 mg) which was prepared in a similar manner to that described in Reference 9 was dissolved in anhydrous methanol (2 ml). To the solution were added triethylamine (100 µl) and mitomycin A (141 mg: 1.0 molar equivalent). The solution was treated in a similar manner to that described in Example 1 to obtain 101 mg of Compound 2 in the form of grayish blue powders with a yield 42%.

EXAMPLE 3

2-(2-benzyloxycarbonylethyl)aminocarbonylthioethylamine (formate: 203 mg) was obtained by subjecting N-triphenylmethyl-2-paranitrophenoxycarbonylthioethylamine (500 mg) and β-alaninebenzylester (p-toluene sulfonate: 308 mg) to similar reactions to those described in References 2 and 4. The product was dissolved in anhydrous methanol (5 ml). To the reaction solution were added triethylamine (200 µl) and mitomycin A (251 mg). The mixture was treated in a similar manner to that described in Example 1 to obtain Compound 3 (156 mg) in the form of grayish blue powders with a yield of 36%.

EXAMPLE 4

2-diethylaminocarbonylthioethylamine (formate: 184 mg) was prepared by subjecting N-triphenylmethyl-2-paranitrophenoxycarbonylthioethylamine (500 mg) and diethylamine (316 μl) to the similar reactions to those described in References 2 and 4. The product was dissolved in anhydrous methanol (4 ml). To the solution were added triethylamine (174 μl) and mitomycin A (273 mg: 0.75 molar equivalent). The reaction solution was treated in a similar manner to that described in Example 1 to obtain Compound 4 (130 mg) in the form of grayish blue powders with a yield of 60%.

EXAMPLE 5

N-triphenylmethyl-2-paranitrophenoxycarbonylthioethylamine (500 mg) and t-butylamine (226 mg) were subjected to similar reactions to those described in References 2 and 4 to prepare 2-t-butylaminocarbonylthioethylamine (crude formate: 239 mg). The product was dissolved in anhydrous methanol (4 ml). To the solution were added triethylamine (1.03 ml) and mitomycin A (300 mg: 0.8 molar equivalent). The reaction solution was treated in a similar manner to that described in Example 1 to obtain Compound 5 (142 mg) in the form of grayish blue powders with a yield of 34%.

EXAMPLE 6

N-triphenylmethyl-2-(paranitrophenoxycarbonylthio)ethylamine (500 mg) and L-prolinemethylester (418 mg) were subjected to similar reactions to those described in References 2 and 4 to prepare 2-((S)-2-methoxycarbonylpyrrolidino)carbonylthioethylamine (formate: 253 mg) which was then dissolved in anhydrous methanol (5 ml). To the solution were then added triethylamine (182 μl) and mitomycin A (304 mg: 0.8 molar equivalents). The reaction solution was treated in a similar manner to that described in Example 1 to obtain Compound 6 (203 mg) in the form of grayish blue powders with a yield of 88%.

EXAMPLE 7

N-triphenylmethyl-2-paranitrophenoxycarbonylthioethylamine (300 mg) and isopropylamine (158 μl) were subjected to similar reactions to those described in References 2 and 4 to prepare 2-isopropylaminocarbonylthioethylamine (crude formate: 139 mg). The product was dissolved in anhydrous methanol (2 ml). To the solution were added triethylamine (205 μl) and mitomycin A (187 mg: 0.8 molar equivalents). The mixture was treated in a similar manner to that described in Example 1 to obtain Compound 7 (94 mg) in the form grayish blue powders with a yield of 37%.

EXAMPLE 8

N-triphenylmethyl-2-paranitrophenoxycarbonylthioethylamine (300 mg) and dimethylamine (145 μl in 40% methanol solution) were subjected to similar reactions to those described in References 2 and 4 to prepare 2-dimethylaminocarbonylthioethylamine (formate: 108 mg). The product was dissolved in anhydrous methanol (2 ml). To the solution were added triethylamine (224 μl) and mitomycin A (204 mg: 0.8 equimolar amount). The reaction solution was treated in a similar manner to that described in Example 1 to obtain Compound 8 (209 mg) in the form of grayish blue powders with a yield of 61%.

EXAMPLE 9

N-triphenylmethyl-2-paranitrophenoxycarbonylthioethylamine (300 mg) and L-valinemethylester (400 mg) were subjected to similar reactions to those described in References 2 and 4 to prepare 2-[(S)-1-methoxycarbonyl-2-methylpropyl]aminocarbonylthioethylamine (crude formate: 98 mg). The product was dissolved in anhydrous methanol (10 ml). To the solution were added triethylamine (338 μl) and mitomycin A (135 mg: 0.8 molar equivalent). The reaction solution was treated in a similar manner to that described in Example 1 to obtain Compound 9 (960 mg) in the form of grayish blue powders with a yield of 28%.

EXAMPLE 10

N-triphenylmethyl-2-(1-phenyl-2-benzyloxycarbonylethyl)aminocarbonylthioethylamine (398 mg) which was produced by the method of Reference 8 was subjected to the reaction carried out in a similar manner to that described in Reference 4 to give 2-(1-phenyl-2-benzyloxycarbonylethyl)aminocarbonylthioethylamine (crude formate: 274 mg). The product was dissolved in anhydrous methanol (4 ml). To the reaction solution were added triethylamine (459 μl) and mitomycin A (189 mg: 0.8 molar equivalent). The solution was treated in a similar manner to that described in Example 1 to obtain Compound 10 (57 mg) in the form of grayish blue powders with a yield of 10%.

EXAMPLE 11

N-triphenylmethyl-2-paranitrophenoxycarbonylthioethylamine (300 mg) and 3-aminopentane (162 mg) were subjected to similar reactions to those described in References 2 and 4 to prepare 2-(1-ethylpropyl)aminocarbonylthioethylamine (formate: 121 mg) which was then dissolved in anhydrous methanol (5 ml). To the reaction solution were added triethylamine (409 μl) and mitomycin A (143 mg: 0.7 molar equivalent). The mixture was treated in a similar manner to that described in Example 1 to obtain Compound 11 (131 mg) in the form of garyish blue powders with a yield of 52%.

EXAMPLE 12

N-triphenylmethyl-2-paranitrophenoxycarbonylthioethylamine (300 mg) and 4-amino-1-benzylpiperidine (355 mg) were subjected to similar reactions to those described in References 2 and 4 to prepare 2-(1-benzylpiperidino-4-yl)aminocarbonylthioethylamine (crude formate: 179 mg) which was then dissolved in anhydrous methanol (4 ml). To the solution were added triethylamine (675 μl) and mitomycin A (129 mg: 0.7 molar equivalent). The reaction solution was treated in a similar manner to that described in Example 1 to obtain grayish blue powders (126 mg) of Compound 12 with a yield of 31%.

EXAMPLE 13

N-triphenylmethyl-2-paranitrophenoxycarbonylthioethylamine (907 mg) and 2-amino-1-benzyloxy-3-methylbutane (formate: 229 mg) were subjected to similar reactions to those described in References 2 and 4 to prepare 2-(1-benzyloxy-methyl-2-methylpropyl)aminocarbonylthioethylamine (crude formate: 130 mg) which was then dissolved in anhydrous methanol (5 ml). To the solution were added triethylamine (266 μl) and mitomycin A (93 mg: 0.7 molar equivalent). The reaction solution was treated in a similar manner to that described in Example 1 to obtain Compound 13 (72 mg) in the form of grayish blue powders with a yield of 44%.

EXAMPLE 14

N-triphenylmethyl-2-paranitrophenoxycarbonylthioethylamine (0.34 g) and L-prolinebenzylamide (0.29 g) were subjected to similar reactions to those described in References 2 and 4 to prepare 2-[(S)-2-benzylaminocarbonylpyrrolidino]carbonylthioethylamine (crude formate: 284 mg). The product was dissolved in anhydrous methanol (4 ml). To the solution were added triethylamine 558 μl) and mitomycin A (224 mg: 0.8 molar equivalent). The solution was treated in a similar manner to that described in Example 1 to obtain grayish blue powders (175 mg) of Compound 14 with a yield of 44%.

EXAMPLE 15

N-triphenylmethyl-2-paranitrophenoxycarbonylthioethylamine (500 mg) and L-proline t-butylester (353 mg) were subjected to similar reaction to that described in Reference 2. The reaction solution was treated with a 50% acetic acid solution (9 ml) at a temperature of 50° C. for 30 minutes to remove the protecting group. The resultant 2-[(S)-2-butoxycarbonylpyrrolidino]carbonylthioethylamine (crude acetate: 127 mg) was dissolved in anhydrous methanol (5 ml). Triethylamine (0.28 ml) and mitomycin A (111 mg: 0.8 molar equivalent) were added to the reaction solution which was then treated in a similar manner to that described in Example 1 to give grayish blue powders (124 mg) of Compound 15 with a yield of 60%.

EXAMPLE 16

N-triphenylmethyl-2-paranitrophenoxycarbonylthioethylamine (0.50 g) and L-prolinebenzylester (hydrochloride: 0.75 g) were subjected to similar reactions to those described in References 2 and 5 to prepare 2-[(S)-2-benzyloxycarbonylpyrrolidino]carbonylthioethylamine (formate: 266 mg). The product was dissolved in anhydrous methanol (4 ml). To the solution were then added triethylamine (556 μl)) and mitomycin A (217 mg: 0.8 molar equivalent). The solution was treated in a similar manner to that described in Example 1 to obtain grayish blue powders (212 mg) of Compound 16 with a yield of 55%.

EXAMPLE 17

N-triphenylmethyl-2-paranitrophenoxycarbonylthioethylamine (0.9 g) and L-prolinemethylamide (trifluoroacetate: 450 mg) were subjected to similar reactions to those described in References 2 and 4 to prepare 2-((S)-2-methylaminocarbonylpyrrolidino)carbonylthioethylamine (crude formate: 514 mg) which was then dissolved in anhydrous methanol (5 ml). Triethylamine (1.3 ml) and mitomycin A (517 mg: 0.8 molar equivalent) were added to the solution which was then treated in a similar manner to that described in Example 1 to obtain Compound 17 (193 mg) in the form of grayish blue crystals with a yield of 33%.

EXAMPLE 18

N-triphenylmethyl-2-paranitrophenoxycarbonylthioethylamine (1.49 g) and L-prolinedimethylamide (trifluoroacetate: 789 mg) were subjected to the reactions described in References 2 and 4 to give 2-[(S)-2-dimethylaminocarbonylpyrrolidino]carbonylthioethylamine (crude formate: 696 mg). The product was dissolved in anhydrous methanol (6.5 ml), to which were then added triethylamine (1.65 ml) and mitomycin A (661 mg: 0.8 molar equivalent). The reaction solution was treated in a similar manner to that described in Example 1 to obtain Compound 18 (512 mg) in the form of grayish blue powders with a yield of 64%.

EXAMPLE 19

N-triphenylmethyl-2-paranitrophenoxycarbonylthioethylamine (611 mg) and L-prolinecarboxylic acid amide (trifluoroacetate: 287 mg) were subjected to the reactions described in References 2 and 4 to give 2-((S)-2-carbamoylpyrrolidino)carbonylthioethylamine (crude formate: 218 mg). The product was dissolved in anhydrous methanol (3.5 ml). To the reaction solution were added triethylamine (576 μl) and mitomycin A (231 mg: 0.8 molar equivalent). The mixture was treated in a similar manner to that described in Example 1 to obtain Compound 19 (235 mg) in the form of grayish blue powders with a yield of 51%.

EXAMPLE 20

N-triphenylmethyl-2-paranitrophenoxycarbonylthioethylamine (666 mg) and L-prolinepivaloyloxymethylester trifluoroacetate: 315 mg) were subjected to similar reactions to those described in References 2 and 4 to prepare 2-[(S)-2-pivaloyloxymethyloxycarbonylpyrrolidino]carbonylthioethylamine (crude formate: 313 mg). The product was added to anhydrous methanol (12 ml). To the solution were added triethylamine (401 μl) and mitomycin A (231 mg: 0.8 molar equivalent). The reaction solution was treated in a similar manner to that described in Example 1 to obtain Compound 20 (136 mg) in the form of grayish blue powders with a yield of 32%.

EXAMPLE 21

N-triphenylmethyl-2-paranitrophenoxycarbonylthioethylamine (300 mg) and pyrrolidine (66 mg) were subjected to similar reactions to those described in References 2 and 4 to prepare 2-pyrrolidylcarbonylthioethylamine (crude formate: 136 mg). The product was dissolved in anhydrous methanol (5 ml). Triethylamine (173 μl) and mitomycin A (195 mg: 0.9 molar equivalent). were added to the reaction solution which was then treated in a similar manner to that described in Example 1 to obtain Compound 21 (132 mg) in the form of grayish blue powders with a yield of 48%.

EXAMPLE 22

N-triphenylmethyl-2-paranitrophenoxycarbonylthioethylamine (300 mg) and benzylamine (202 μl) were subjected to similar reactions to those described in References 2 and 4 to prepare 2-benzylaminocarbonylthioethylamine (crude formate: 256 mg). The product was dissolved in anhydrous methanol (5 ml). To the solution were added triethanolamine (354 μl) and mitomycin A (142 mg: 0.8 molar equivalent). The reaction solution was treated in a similar manner to that described in Example 1 to obtain Compound 22 (38 mg) in the form of grayish blue powders with a yield of 18%.

EXAMPLE 23

N-triphenylmethyl-2-paranitrophenoxycarbonylthioethylamine (300 mg) and ethylamine (hydrochloride: 153 mg) were subjected to similar reactions to those described in References 2 and 4 to prepare 2- ethylaminocarbonylthioethylamine (crude formate: 247 mg) which was then dissolved in anhydrous methanol (5 ml). To the solution were added triethylamine (388 μl) and mitomycin A (156 mg: 0.8 molar equivalent). The reaction solution was treated in a similar manner to that described in Example 1 to obtain Compound 23 (126 mg) in the form of grayish blue powders with a yield of 61%.

EXAMPLE 24

N-triphenylmethyl-2-paranitrophenoxycarbonylthioethylamine (300 mg) and isobutylamine (185 μl) were subjected to similar reactions to those described in References 2 and 4 to give 2-isobutylaminocarbonylthioethylamine (crude formate: 256 mg) which was then dissolved in anhydrous methanol (5 ml). Triethylamine (376 μl) and mitomycin A (151 mg: 0.8 molar equivalent) were added to the solution. The reaction solution was treated in a similar manner to that described in Example 1 to obtain Compound 24 (71 mg) in the form of grayish blue powders with a yield of 33%.

EXAMPLE 25

N-triphenylmethyl-2-methylaminothiocarbonylthioethylamine (0.89 g) which was prepared by the method of Reference 5 was subjected to a similar reaction to that described in Reference 4 to prepare 2-methylaminothiocarbonylthioethylamine (crude formate: 223 mg). The product was dissolved in anhydrous methanol (7 L ml). Triethylamine (732 μl) and mitomycin A (316 mg: 0.8 molar equivalent) were added to the reaction solution which was then treated in a similar manner to that described in Example 1 to obtain Compound 25 (233 mg) in the form of grayish blue powders with a yield of 44%.

EXAMPLE 26

2-methylaminothiocarbonylthioethylamine (crude formate: 223 mg) which was prepared in a similar manner to that described in Example 25 was dissolved in anhydrous methanol (7 ml). Triethylamine (316 μl) and mitomycin B (316 mg: 0.8 molar equivalent) were added to the reaction solution which was then treated in a similar manner to that described in Example 1 to obtain Compound 26 (53 mg) in the form of grayish blue powders with a yield of 10%.

EXAMPLE 27

N-triphenylmethyl-2-paranitrophenoxycarbonylthioethylamine (300 mg) and n-propylamine (153 μl) were subjected to similar reactions to those described in References 2 and 4 to prepare 2-n-propylaminocarbonylthioethylamine (crude formate: 218 mg). The product was dissolved in anhydrous methanol (5 ml). To the solution were added triethylamine (340 μl) and mitomycin A (137 mg: 0.8 molar equivalent). The reaction solution was treated in a similar manner to that described in Example 1 to obtain Compound 27 (108 mg) in the form of grayish blue powders with a yield of 58%.

EXAMPLE 28

N-triphenylmethyl-2-paranitrophenoxycarbonylthioethylamine (300 mg) and n-butylamine (184 μl) were subjected to similar reactions to those described in References 2 and 4 to prepare 2-n-butylaminocarbonylthioethylamine (crude formate: 245 mg). The product was dissolved in anhydrous methanol (5 ml). Triethylamine (533 μl) and mitomycin A (154 mg: 0.8 molar equivalent) were added to the reaction solution which was then treated in a similar manner to that described in Example 1 to obtain Compound 28 (53 mg) in the form of grayish blue powders with a yield of 24%.

EXAMPLE 29

N-triphenylmethyl-2-(paranitrophenoxycarbonylthio)ethylamine (600 mg) and cyclohexylamine (568 μl) were subjected to similar reactions to those described in References 2 and 4 to prepare 2-cyclohexylaminocarbonylthioethylamine (crude formate: 380 mg). The product was dissolved in anhydrous methanol (7 ml). Triethylamine (519 μl) and mitomycin A (206 mg: 0.8 molar equivalent) were added to the reaction solution which was then treated in a similar manner to that described in Example 1 to obtain Compound 29 (156 mg) in the form of grayish blue powders with a yield of 51%.

EXAMPLE 30

N-triphenylmethyl-2-paranitrophenoxycarbonylthioethylamine (300 mg) and sec-butylamine (188 μl) were subjected to similar reactions to those described in References 2 and 4 to give 2-sec-butylaminocarbonylthioethylamine (crude formate: 227 mg). The product was dissolved in anhydrous methanol (5 ml). Triethylamine (342 μl) and mitomycin A (137 mg: 0.8 molar equivalent) were added to the reaction solution which was then treated in a similar manner to that described in Example 1 to obtain Compound 30 (94 mg) in the form of grayish blue powders with a yield of 49%.

EXAMPLE 31

N-triphenylmethyl-2-paranitrophenoxycabonylthioethylamine (300 mg) and L-proline (356 mg) were subjected to similar reactions to those described in References 2 and 4 to give 2-((S)-2-carboxypyrrolidino)carbonylthioethylamine (crude formate: 216 mg). The product was dissolved in anhydrous methanol (5 ml). Triethylamine (573 μl) and mitomycin A (287 mg: 1.0 molar equivalent) were added to the reaction solution which was then treated in a similar manner to that described in Example 1 to obtain Compound 31 (112 mg) in the form of grayish blue powders with a yield of 51%.

EXAMPLE 32

N-triphenylmethyl-2-paranitrophenoxycarbonylthioethylamine (675 mg) and D-proline methylester (0.18 g) were subjected to similar reactions to those described in References 2 and 4 to give 2-[(R)-2-methoxycarbonylpyrrolidino]carbonylthioethylamine (crude formate: 336 mg). The product was dissolved in anhydrous methanol (6 ml). To the solution were added triethylamine (1.01 ml) and mitomycin A (338 mg: 0.8 molar equivalent). The solution was then treated in a similar manner to that described in Example 1 to obtain Compound 32 (286 mg) in the form of grayish blue powders with a yield of 43%.

EXAMPLE 33

N-triphenylmethyl-2-paranitrophenoxycarbonylthioethylamine (300 mg) and morpholine (162 μl) were subjected to similar reactions to those described in References 2 and 4 to give 2-morpholinocarbonylthioethylamine (crude formate: 134 mg). The product was dissolved in anhydrous methanol (3 ml). To the reaction solution were added triethylamine (486 μl) and mitomycin A (195 mg: 0.8 molar equivalent). The mixture was treated in a similar manner to that described in Example 1 to obtain Compound 33 (176 mg) in the form of grayish blue powders with a yield of 50%.

EXAMPLE 34

P-nitrochloroformate (581 mg). 1-t-butoxycarbonyl-1-methylethylamine (formate: 493 mg) and N-triphenylmethylcysteamine (967 mg) were subjected to a similar reaction to that described in Reference 8. From the reaction product, triphenylmethyl was removed by the method described in Reference 4 to prepare 2-(1-t-butoxycarbonyl-1-methylethyl)aminocarbonylthioethylamine (crude fomate: 110 mg). The product was dissolved in anhydrous methanol (2 ml). To the solution were added triethylamine (247 μl) and mitomycin A (99 mg: 0.8 molar equivalent). The solution was treated in a similar manner to that described in Example 1 to obtain Compound 34 (74 mg) in the form of grayish blue powders with a yield of 36%.

EXAMPLE 35

N-triphenylmethyl-2-paranitrophenoxycarbonylthioethylamine (300 mg) and methylhydrazine (99 μl) were subjected to similar reactions to those described in References 2 and 4 to prepare 2-(1-methyl-2-formylhydrazino)carbonylthioethylamine (formate: 204 mg). The product was dissolved in anhydrous methanol (2 ml). Triethylamine (288 μl) and mitomycin A (115 mg: 0.8 molar equivalent) were added to the reaction solution which was then treated in a similar manner to that described in Example 1 to obtain Compound 35 (107 mg) in the form of grayish blue powders with a yield of 56%.

EXAMPLE 36

N-triphenylmethyl-2-(paranitrophenoxycarbonylthio) ethylamine (300 mg) and methylhydrazine (99 μl) were subjected to similar reactions to those described in References 2 and 4 to prepare 2-(1-methyl-2-formylhydrazino)carbonylthioethylamine (formate: 204 mg). The product was dissolved in anhydrous methanol (2 ml). Triethylamine (288 μl) and mitomycin B (115 mg: 0.8 molar equivalent) were added to the reaction solution which was then treated in a similar manner to that described in Example 1 to obtain Compound 36 (100 mg) in the form of grayish blue powders with a yield of 52%.

EXAMPLE 37

Cyclohexylisothiocyanate (0.2 ml) and N-triphenylmethylcysteamine (150 mg) were subjected to the reaction described in Reference 5. From the reaction product, triphenylmethyl was removed by the method described in Reference 4 to obtain 2-cyclohexylaminothiocarbonylthioethylamine (crude formate: 92 mg). The product was dissolved in anhydrous methanol (2 ml). Triethylamine (0.24 ml) and mitomycin A (97 mg: 0.8 molar equivalent) were added to the reaction solution which was then treated in a similar manner to that described in Example 1 to obtain Compound 37 (54 mg) in the form of grayish blue powders with a yield of 36%.

EXAMPLE 38

2-chlorohexylthiocarbonylthioethylamine (crude formate: 92 mg) was prepared in a similar manner to that described in Example 37. The product was dissolved in anhydrous methanol (2 ml), to which were then added triethylamine (0.24 ml) and mitomycin B (97 mg: 0.8 molar equivalent). The reaction solution was treated in a similar manner-to that described in Example 1 to obtain Compound 38 (59 mg) in the form of grayish blue powders with a yield of 39%.

EXAMPLE 39

Ethylisocyanate (329 μl) and N-triphenylmethylcysteamine (400 mg) was subjected to the reaction of Reference 5. From the product, triphenylmethyl was removed by the method described in Reference 4 to give 2-ethylaminothiocarbonylthioethylamine (crude formate: 0.21 g). The product was dissolved in anhydrous methanol (8 ml). To the solution was added triethylamine (1.4 ml) and mitomycin A (282 mg: 0.8 molar equivalent). The solution was treated in a similar manner to that described in Example 1 to obtain Compound 39 (110 mg) in the form of grayish blue powders with a yield of 23%.

EXAMPLE 40

N-propylisothiocyanate (389 μl) and N-triphenylmethylcysteamine (400 mg) were subjected to the reaction described in Reference 4 to obtain 2-n-propylaminothiocarbonylthioethylamine (crude formate: 0.22 g). The product was dissolved in anhydrous methanol (4 ml). Triethylamine (696 μl) and mitomycin A 8279 mg: 0.8 molar equivalent) were added to the reaction solution which was then treated in a similar manner to that described in Example 1 to obtain Compound 40 (80 mg) in the form of grayish blue powders with a yield of 16%.

EXAMPLE 41

N-triphenylmethyl-2-paranitrophenoxycarbonylthioethylamine (300 mg) and 4-benzylpiperidine (327 μl) were subjected to similar reactions to those described in References 2 and 4 to give 2-(4-benzylpiperidino)carbonylthioethylamine (crude formate: 210 mg). The product was dissolved in anhydrous methanol (3.5 ml). Triethylamine (432 μl) and mitocyin A (151 mg: 0.7 molar equivalent) were added to the solution which was then treated in a similar manner to that described in Example 1 to obtain Compound 41 (300 mg) in the form of grayish blue powders with a yield of 81%.

EXAMPLE 42

N-triphenylmethyl-2-paranitrophenoxycarbonylthioethylamine (300 mg) and piperidine (184 μl) were subjected to similar reations to those described in References 2 and 4 to give 2-piperidinocarbonylthioethylamine (crude formate: 137 mg). The product was dissolved in anhydrous methanol (3 ml). To the solution were added triethylamine (432 μl) and mitomycin A (151 mg: 0.7 molar equivalent). The solution was treated in a similar manner to that described in Example 1 to obtain Compound 42 (0.21 mg) in the form of grayish blue powders with a yield of 74%.

EXAMPLE 43

N-triphenylmethyl-2-paranitrophenoxycarbonylthioethylamine (300 mg) and 4-hydroxypiperidine (219 mg) were subjected to similar reactions to those described in References 2 and 4 to give 2-(4-hydroxypiperidino)carbonylthioethylamine (crude formate: 185 mg) which was then dissolved in anhydrous methanol (3 ml). To the reaction solution were added triethylamine (515 μl) and mitomycin A (207 mg: 0.8 molar equivalent). The reaction solution was treated in a similar manner to that described in Example 1 to obtain Compound 43 (325 mg) in the form of grayish blue powders with a yield of 84%.

EXAMPLE 44

N-triphenylmethyl-2-paranitrophenoxycarbonylthioethylamine (350 mg) and 3-hydroxy-L-prolinemethylester (hydrochloride: 0.23 g) were subjected to similar reactions to those described in References 2 and 4 to give 2-[(S)-2-methoxycarbonyl-(RS)-4-hydroxypyrrolidino]-carbonylthioethylamine (formate: 171 mg) which was then dissolved in anhydrous methanol (3 ml). Triethylamine (405 μl) and mitomycin A (203 mg: 1.0 molar equivalent) were added to the reaction solution which was then treated in a similar manner to that described in Example 1 to obtain Compound 44 (210 mg) in the form of grayish blue powders with a yield of 64%.

EXAMPLE 45

N-triphenylmethyl-2-paranitrophenoxycarbonylthioethylamine (1.0 g) and L-proline (713 mg) were subjected to a similar reaction described in Reference 2 to give N-triphenylmethyl-2-[(S)-2-carboxypyrrolidino)-carbonylthioethylamine (475 mg) which was then dissolved in a mixture of anhydrous dimethylformamide (1.5 ml) and anhydrous acetonitrile (4 ml). After addition of dicyclohexylcarbodiimide (256 mg) and 4-aminohenol (256 mg), the reaction solution was stirred at room temperature for 5 hours and was then concentrated under reduced pressure. The concentrated solution was dissolved in chloroform (50 ml), followed by washing in turns with an aqueous solution of 10% citric acid, a saturated sodium bicarbonate solution, water and a saturated solution of sodium chloride. The chloroform layer was dried by use of anhydrous sodium sulfate and was then concentrated under reduced pressure. The residual substance was purified by silica gel column chromatography using a solvent system of chloroform/methanol (20:1 v/v) to obtain N-triphenylmethyl-2-[(S)-2-(4-hydroxyphenyl)aminocarbonylpyrrolidino]-carbonylthioethylamine (0.45 g: yield 79.0%). From the product triphenylmethyl was removed in a similar manner to that described in Example 4 to produce 2-(S)-2-4-hydroxyphenyl)aminocarbonylpyrrolidino]carbonylthioethylamine (crude formate: 445 mg). This product was dissolved in anhydrous methanol (7 ml). To the reaction solution were added triethylamine (873 μl) and mitomycin A (380 mg: 0.87 molar equivalent). The mixture was treated in a similar manner to that described in Example 1 to obtain Compound 45 (160 mg) in the form of grayish blue powders with a yield of 39%.

EXAMPLE 46

P-nitrophenylchloroformate (0.50 g), 3-amino-2,4-dimethylpentane (0.60 g) and N-triphenylmethylcysteamine (0.67 g) were subjected to the reaction described in Reference 8 to give N-triphenylmethyl-2-(1-isopropyl-2-methylpropyl)aminocarbonylthioethylamine (0.81 g). The product was treated in a similar manner to that described in Reference 4 to remove triphenylmethyl. The resultant 2-(1-isopropyl-2-methylpropyl)aminocarbonylthioethylamine (crude formate) was dissolved in anhydrous methanol (10 ml) without aftertreatment. To the reaction solution were added triethylamine (1.23 ml) and mitomycin A (0.49 g). The mixture was treated in a similar manner to that described in Example 1 to obtain Compound 46 (0.52 g) in the form of grayish blue powders with a yield of 69%.

EXAMPLE 47

P-nitrophenylchloroformate (0.50 g). trans-2-cis-6-dimethylcyclohexylamine (630 mg) and N-triphenylmethylcysteamine (0.88 g) were subjected to the reaction described in Reference 8 to give N-triphenylmethyl-trans-2-cis-6-dimethylcyclohexylaminocarbonylthioethylamine (0.72 g). from which triphenylmethyl was removed in a similar manner to that described in Reference 4. The resultant trans-2-cis-6-dimethylcyclohexylaminocarbonylthioethylamine (crude formate) was dissolved in anhydrous methanol (6 ml) without aftertreatment. Triethylamine (1.09 ml) and mitomycin A (410 mg) were added to the reaction solution which was then treated in a similar manner to that described in Example 1 to obtain Compound 47 (0.46 g) in the form of grayish blue powders with a yield of 72%.

EXAMPLE 48

N-triphenylmethyl-2-paranitrophenoxycarbonylthioethylamine (0.58 g) and 2-amino-1-tert-butyldimethylsilyloxy-3-methylbutane (acetate: 0.52 g) were subjected to the reactions described in References 2 and 4 to give 2-(1-hydroxymethyl-2-methylpropyl)aminocarbonylthioethylamine (formate: 1.03 g). The product (0.83 g) was dissolved in anhydrous methanol (10 ml), to which were then added triethylamine (0.91 ml) and mitomycin A (372 mg: 0.82 molar equivalent). The reaction solution was treated in a similar manner to that described in Example 1 to obtain Compound 48 (290 mg) in the form of grayish blue powders with a yield of 52%.

EXAMPLE 49

N-triphenylmethyl-2-paranitrophenoxycarbonylthioethylamine (500 mg) and 2-(2-aminoethyl)pyridine (375 μl) were subjected to the reactions described in References 2 and 4 to give 2-(2-pyridyl)ethylaminocarbonylthioethylamine (crude formate: 218 mg). The product (190 mg) was dissolved in anhydrous methanol (3 ml), to which were then added triethylamine (490 μl) and mitomycin A (245 mg: 1.0 molar equivalent). The reaction solution was treated in a similar manner to that described in Example 1 to obtain Compound 49 (297 mg) in the form of grayish blue powders with a yield of 78%.

EXAMPLE 50

In a similar manner to that described in Reference 5, diphenylmethylisocyanate (176 mg) and N-triphenylmethylcysteamine (300 mg) were subjected to the reaction. Then triphenylmethyl was removed from the reaction product in a similar manner to that described in Reference 4 to give 2-diphenylmethylaminothiocarbonylthioethylamine (0.27 g) which was then dissolved in anhydrous methanol (4.5 ml). Triethylamine (546 μl) and mitomycin A (218 mg: 0.8 molar equivalent) were added to the reaction solution and treated in a similar manner to that described in Example 1 to obtain Compound 50 (123 mg) in the form of grayish blue powders with a yield of 32%.

Reference 1

N-triphenylmethyl-2-paranitrophenoxycarbonylthioethylamine

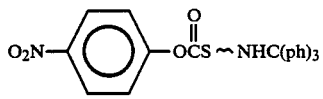

Paranitrophenylchloroformate (2.71 g) was dissolved in anhydrous tetrahydrofuran (47 ml). To this solution were added triethylamine (20 ml: 1.1 molar equivalent) and dimethylaminopyridine (3.2 mg: 0.002 equimolar amount) while cooling with ice. To this solution was then added with stirring drops of N-triphenylcysteamine (4.59 g: 1.1 equimolar amount) which was dissolved in anhydrous tetrahydrofuran (30 ml). The reaction solution was stirred at room temperature for 4 hours and was filtered to remove impurities. The filtrate was concentrated under reduced pressure. The residue was dissolved in chloroform (50 ml). The chloroform solution was well washed with water and a saturated solution of sodium chloride. The chloroform layer was dried by using anhydrous sodium sulfate and concentrated under reduced pressure. To the residue was added a mixture of ethyl acetate and n-hexane (1:5 v/v) to obtain the desired substance (3.70 g) in the form of colourless crystals with a yield of 59%

$^1$H-NMR ($\delta$, CDCl$_3$, 60 MHz): 8.27 (2H d), 7.58~7.12 (17H, m). 3.09 (2H t), 2.49 (2H t), 1.78 (1H m).

Reference 2 (Step 2)

N-triphenylmethyl-2-methylaminocarbonylthioethylamine

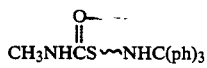

N-triphenylmethyl-2-paranitrophenoxycarbonylthioethylamine (483 mg) which was prepared by the method of Reference 1 was dissolved in anhydrous tetrahydrofuran (4 ml), to which were then dropwise added methylamine (hydrochloride: 203 mg: 3 molar equivalent) and triethylamine (303 mg: 3 molar equivalent). Then the reaction solution was stirred for 10 hours at room temperature and was then concentrated under reduced pressure. The residue was dissolved in chloroform and well washed with water and a saturated solution of sodium chloride. The material was dried by the use of anhydrous sodium sulfate and concentrated under reduced pressure. The residue was purified by silica gel chromatography using a solvent system of chloroform/acetone (40: 1 v/v) to obtain the desired substance (327 mg) with a yield of 86%.

$^1$H-NMR ($\delta$, CDCl$_3$, 60 MHz): 7.10~7.55 (15H m), 3.02 (2H q), 2.83 (3H d) 2.40 (2Ht), 1.86 (1H bs).

Reference 3 (Step 4)

N-triphenylmethyl-2-methylaminocarbonylthioethylamine

Methylisocyanate (243 mg) was dissolved in anhydrous dichloromethane (5 ml). To the solution were added N-triphenylmethylcysteamine (3.19 g: 0.33 equimolar amount) while cooling with ice. The reaction solution was stirred at room temperature for 4 hours and was concentrated under reduced pressure. The residue was dissolved in chloroform (50 ml), and the chloroform solution was well washed with water and a saturated solution of sodium chloride. Anhydrous sodium sulate was used to dry the chloroform layer which was then concentrated under reduced pressure. The residue was purified by silica gel chromatography using a solvent system of hexane/ethyl acetate (5:1 v/v) to obtain the desired substance (297 mg) with a yield of 79%.

Reference 4 (Step 5)

2-methylaminocarbonylthioethylamine (formate)

To N-triphenylmethyl-2-methylaminocarbonylthioethylamine (306 mg) which was prepared by the method of Reference 2 was added formic acid (98%; 5 ml). The reaction solution was stirred at a temperature of 50° C. for 30 minutes and was then concentrated under reduced pressure. The resultant residue was purified without after-treatment by silica gel chromatography using a solvent system of chloroform/methanol/water (6:5:1 v/v) to obtain 139 mg of the desired product with a yield of 95%.

$^1$H-NMR ($\delta$, D$_2$O, 60 MHz): 8.40 (1H s), 3.1 (4H s), 2.77 (3H s).

IR (Neat) cm$^-$: 3150, 2450, 1580, 1380, 1340, 1225, 1160, 1025.

MASS: 134 (M$^+$), 105 (M$^+$ −29).

Reference 5 (Step 4)

N-triphenylmethyl-2-methylaminocarbonylthioethylamine

Methylthioisocyanate (210 mg) was dissolved in anhydrous dichloromethane (5 ml). To the solution were added N-triphenylmethylcysteamine (1.00 g: 1.1 molar equivalent) while cooling with ice. The reaction solution was stirred at room temperature for 30 minutes and was concentrated under reduced pressure. The residue was dissolved in chloroform (50 ml) and well washed with water and a saturated solution of sodium chloride. The chloroform layer was dried by using anhydrous sodium sulfate and concentrated under reduced pressure. The residue was purified by silica gel chroomatography using a solvent system of hexane/ethyl acetae (5:1 v/v) to obtain the desired substance (0.89 g) with a yield of 79%.

$^1$H-NMR ($\delta$, CDCl$_3$, 60 MHz): 7.49~7.06 (15H m), 3.13 (2H t), 2.48 (2H t), 2.00 (3H s),

Reference 6 (Step 6)

2-chloromethyloxycarbonylaminopropionic acid t-butyl ester

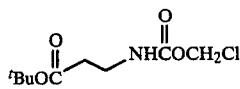

β-alanine t-butylester (316 mg) was dissolved in methylene chloride (2 ml). To this solution were added triethylamine (333 μl: 1.1 molar equivalent) and chloromethylchloroformate (309 mg: 1.1 molar equivalent). The mixture was stirred for 20 minutes while cooling with ice. The reaction solution was concentrated under reduced pressure and was then dissolved in chloroform (20 ml), followed by washing well with water and a saturated solution of sodium chloride. Anhydrous sodium sulfate was applied to dry the chloroform layer which was then concentrated under reduced pressure. The concentrate was purified by silica gel chromatography using a solvent system of chloroform/methanol (200:1 v/v) to obtain the desired substance (394 mg) with a yield of 76%.

$^1$H-NMR (δ, CDCl$_3$, 60 MHz): 5.69 (2H s), 3.43 (2H q), 2.45 (2H t), 1.43 (9H s).

IR (Neat, cm$^{-1}$): 2980, 1720, 1155, 1255.

Reference 7 (Step 7)

N-triphenylmethyl-2-(2-t-butoxycarbonylethyl)aminocarbonyloxymethylthioethylamine

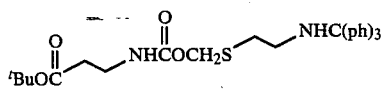

2-chloromethyloxycarbonylaminopropionic acid t-butylester (394 mg) which was prepared by the process described in Reference 6 was dissolved in acetone (5 ml). To the solution was added sodium iodide (273 mg: 1.1 molar equivalent) in a dark place. The mixture was stirred at room temperature for 9 hours. After this, to the mixture were added N-triphenylmethylcysteamine (788 mg: 1.5 molar equivalent) and silver carbonate (506 mg: 1.1 molar equivalent). The reaction solution was stirred for 18 hours at room temperature and filtered. The filtrate was concentrated under reduced pressure and was then dissolved in chloroform. The solution was well washed with water and a saturated solution of sodium chloride. The chloroform layer was dried by using anhydrous sodium sulfate and concentrated under reduced pressure. The residue was purified by silica gel chromatography using a solvent system of chloroform/methanol (200:1 v/v) to obtain the desired substance (220 mg) with a yield of 25%.

$^1$H-NMR (δ, CDCl$_3$, 60 MHz): 7.55~7.10 (15H m), 5.70 (1H s), 5.03 (2H s). 3.38 (2H t), 3.28 (2H t), 2.48 (2H t) 2.00 (1H b), 1.44 (9H s), 2.42 (2H t).

Reference 8 (Step 3)

3-(2-triphenylmethylaminoethyl)thiocarbonylamino-3-phenylpropionic acid benzylester

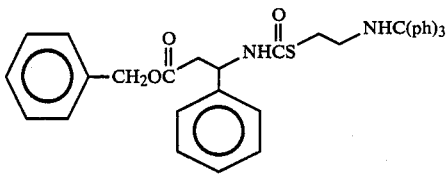

P-nitrophenylchloroformate (0.42 g) was dissolved in anhydrous methylene chloride (5 ml). To the solution was dropwise added 2-amino-2-phenylpropionic acid benzylester (0.80 g) which was dissolved in anhydrous methylene chloride (5 ml). The mixture was stirred at a temperature of 0° C. for 30 minutes. The reaction solution was dissolved in chloroform (50 ml) and washed well with water and a saturated solution of sodium chloride. Anhydrous sodium sulfate was applied to dry the chloroform layer, which was then concentrated under reduced pressure. The residue was added to a mixture of ethyl acetate and n-hexane (1:5 v/v) for crystallization to produce colourless crystals of 3-p-nitrophenoxycarbonylamino-3-phenyl propionic acid benzylester (4.09 mg) with a yield of 50%. Anhydrous chloroform (5 ml) was used to dissolve the resultant crystals (4.09 mg). To the solution were added N-triphenylmethylcysteamine (385 mg: 1.2 molar equivalent) and triethylamine (168 μl:1.2 molar equivalent). After stirring for 3 hours at room temperature, the reaction solution was concentrated under reduced pressure to give a residue. The residue was then dissolved in chloroform (50 ml). The solution was well washed with water and a saturated solution of sodium chloride. The chloroform layer was dried with anhydrous sodium sulfate and was then concentrated under reduced pressure. The residue was purified by silica gel chromatography using a solvent system of n-hexane/ethyl acetate (5:1 v/v) to obtain the desired substance (398 mg) with a yield of 68%.

1H-NMR (δ, CDCl$_3$, 60 MHz): 7.50~7.05 (25H m), 6.40 (1H d), 4.98 (2H s). 2.92 (5H m), 2.37 (2H t).

Reference 9

2-(2-t-butoxycarbonylethyl)aminocarbonyloxymethylthioethylamine (acetate)

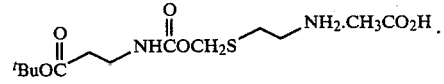

N-triphenylmethyl 2-(t-butoxycarbonylethyl)aminocarbonyloxymethylthioethylamine (177 mg) which was produced by the process described in Reference 5 was dissolved in an aqueous solution of acetic acid (50%: 2 ml). After stirring at a temperature of 50° C. for 1.5 hours, the reaction solution was concentrated under reduced pressure to give a residue. The residue was purified by silica gel chromatography using a solvent system of chloroform/methanol/water (6:4:1 v/v) to obtain the desired product (113 mg) with a yield of 98%.

$^1$H-NMR (δ, CDCl$_3$, 60 MHz): 6.60 (2H bs), 5.13 (2H s), 3.50 (2H t), 3.00 (4H m), 1.43 (9H s).

TABLE 4

| No. | ¹H—NMR (δ, CDCl₃, 270MHz) |
|---|---|
| 1 | 6.46(1H b),5.55(1H b),4.82(2H b),4.71(1H dd),4.48(1H t),4.27(1H d),3.79(2H q),3.60(2H dd),3.51(1H dd),3.21(2H s),3.11(2H t),2.88(3H d),2.81(1H dd),1.98(3H s) |
| 2 | 6.56(1H b),5.70(1H b),5.18(2H s),4.84(2H b),4.71(1H dd),4.50(1H t),4.28(1H d),3.79(2H q),3.61(1H dd),3.53(2H dd),3.46(1H dd),3.21(3H s),2.90(2H t),2.90(1H d),2.82(1H b),2.47(2H t),2.01(3H s),1.45(9H s) |
| 3 | 7.53(5H s),6.48(1H b),6.17(1H b),5.14(2H s),4.89(2H b),4.70(1H d),4.47(1H t),4.25(1H d),3.77(2H q),3.57(3H m),3.20(3H s),3.09(2H t),2.89(1H d),2.81(1H d),2.63(2H t) |
| 4 | 6.57(1H b),4.77(2H b),4.71(1H dd),4.49(1H t),4.28(1H d),3.80(2H q),3.60(1H dd),3.51(1H dd),3.48–3.26(4H m),3.20(3H s),3.13(2H t),2.89(1H d),2.85(1H dd),1.99(3H s) |
| 5 | 6.49(1H b),5.28(1H b),4.77(2H b),4.70(1H b),4.49(1H t),4.28(1H d),3.77(2H q),3.60(1H dd),3.51(1H dd),3.20(3H s),3.06(2H t),2.89(1H d),2.81(1H d) |
| 6 | 6.49(1H b),4.79(2H b),4.71(1H dd),4.27(1H d),3.77(2H dd),3.75(3H s),3.59(1H dd),3.53–3.50(3H b),3.16(2H d),3.06(1H dd),2.89(1H d),2.81(1H d) |
| 7 | 6.51(1H bs),5.38(1H bs),4.86(2H bs),4.70(1H dd),4.48(1H t),4.27(1H d),4.05(1H bs),3.78(2H q),3.69(1H dd),3.51(1H dd),3.20(3H s),3.10(2H t),2.89(1H d),2.82(1H d),1.99(3H s),1.19(6H d) |
| 8 | 6.55(1H b),4.86(2H b),4.70(1H dd),4.48(1H t),4.27(1H d),3.79(2H q),3.60(1H dd),3.51(1H dd),3.20(3H s),3.11(2H t),3.02(6H s),2.89(1H d),2.82(1H d) |
| 9 | 6.47(1H b),6.03(1H d),4.81(2H b),4.70(1H dd),4.49(1H t),4.55(1H b),4.27(1H d),3.76(2H q),3.76(2H q),3.60(1H dd),3.51(1H dd),3.21(3H s),3.10(2H t),2.89(1H d),2.81(1H d),1.20–1.13(1H m),1.98(3H s),0.94(6H dd) |
| 10 | 7.33–7.19(10H m),6.41(5H b),5.05(2H s),4.71(1H dd),4.50(1H t),4.27(1H d),3.76(2H q),3.67(1H t),3.59(1H dd),3.48(1H dd),3.20(3H s),3.09(2H t),2.96(2H dd),2.88(1H d),2.80(1H d),1.95(3H s) |
| 11 | 6.50(1H b),5.19(1H b),4.85(2H b),4.70(1H dd),4.48(1H t),4.27(1H d),3.79(2H q),3.60(1H dd),3.51(1H dd),3.20(3H s),3.11(2H t),2.90(1H d),2.82(1H d),1.99(3H s),1.62–1.49(2H m),1.48–1.31(2H m),0.91(6H t) |
| 12 | 7.34–7.30(5H m),6.50(1H b),5.79(1H b),4.95(2H b),4.71(1H dd),4.46(1H t),4.26(1H d),3.78(2H q),3.59(2H s),3.51(1H dd),3.60(1H dd),3.20(3H s),3.09(2H t),2.89(1H d),2.90(2H m),2.81(1H d),2.25(2H m),1.98(3H s),2.00(2H m),1.60(2H m) |
| 13 | 7.32(5H b),6.50(1H b),5.68(1H b),4.74(2H b),4.70(1H dd),4.50(3H m),4.27(1H d),3.78(3H m),3.59(1H dd),3.53(1H m),3.48(2H m),3.20(3H s),3.10(2H t),2.87(1H d),2.80(1H d),1.98(3H s),1.95(2H m),0.91(6H d) |
| 14 | 7.26(5H s),4.74(2H b),4.66(1H dd),4.45(5H m),4.20(1H d),3.74–3.52(7H m),3.19(3H s),3.15(2H t),2.88(1H d),1.96(3H s),2.10–1.90(4H m) |
| 15 | 6.49(1H b),4.79(2H b),4.73(1H dd),4.49(1H t),4.42(1H dd),4.27(1H d),3.78(2H q),3.59(1H dd),3.51(1H dd),3.20(3H s),3.17(2H t),3.05(1H dd),2.89(1H d),2.82(1H d),1.98(3H s),1.46(1H s) |
| 16 | 7.35(5H s),6.48(1H b),5.18(2H q),4.76(2H b),4.71(1H dd),4.59(1H d),4.49(1H dd),4.27(1H d),3.76(2H q),3.60(1H dd),3.20(3H s),3.10(2H m),2.88(1H d),2.80(1H d),2.2–2.0(4H m),1.97(3H s) |
| 17 | 6.78(1H b),6.54(1H b),4.83(2H b),4.79(1H dd),4.51(1H dd),4.47(1H t),4.26(1H d),3.79(2H b),3.59(1H dd),3.52(1H dd),3.21(3H s),2.90(1H d),2.82(3H t),2.82(1H d),1.99(3H s),2.1–1.90(4H m) |
| 18 | 6.52(1H b),4.87(1H dd),4.80(2H b),4.48(1H t),4.27(1H d),3.78(2H q),3.59(1H dd),3.51(1H dd),3.21(3H s),3.12(3H s),3.00(2H t),2.97(3H s),2.89(1H d),2.82(1H d),2.19–1.90(4H m),1.97(3H s) |
| 19 | 6.84(1H b),6.71(1H b),6.10(1H b),5.04(2H b),4.78(1H dd),4.62(1H d),4.37(1H t),4.27(1H d),3.88(2H m),3.76(2H m),3.56(1H dd),3.51(1H d),3.20(3H s),3.18–3.06(2H m),2.91(1H d),2.83(1H d),2.10–2.00(4H m),2.00(3H s) |
| 20 | 6.47(1H b),5.86(1H d),5.73(1H d),4.75(2H b),4.71(1H dd),4.54(1H dd),4.50(1H t),4.27(1H d),3.78(2H q),3.60(1H dd),3.51(1H dd),3.50(2H m),3.21(3H s),3.12(1H t),3.06(1H t),2.89(1H d),2.82(1H d),2.0(4H m),1.98(3H s),1.15(9H s) |
| 21 | 6.56(1H b),4.78(2H b),4.71(1H dd),4.49(1H t),4.28(1H d),3.80(2H q),3.60(1H dd),3.38(4H m),3.38(2H t),3.20(3H s),3.12(2H t),2.89(1H d),2.81(1H dd),2.00(3H s),1.96–1.57(4H m) |
| 22 | 7.26(5H m),6.45(1H b),5.77(1H b),4.72(2H b),4.72(1H dd),4.49(1H t),4.48(2H s),4.26(1H d),3.80(2H q),3.60(1H dd),3.51(1H dd),3.20(3H s),3.14(2H t),2.88(1H d),2.80(1H d),1.99(3H s) |
| 23 | 6.50(1H b),5.58(1H b),4.89(2H b),4.70(1H dd),4.47(1H t),4.27(1H d),3.79(2H q),3.59(1H dd),3.51(1H d),3.38–3.29(2H m),3.20(3H s),3.10(2H t),2.90(1H d),2.82–2.80(1H m),1.99(3H s),1.17(3H t) |
| 24 | 6.48(1H b),5.53(1H b),4.82(2H b),4.71(1H dd),4.48(1H t),4.27(1H d),3.79(2H q),3.60(1H dd),3.51(1H d),3.20(3H s),3.12(4H q),2.89(1H d),2.82(1H d),1.98(3H s),1.87–1.50(1H m),0.92(6H d) |
| 25 | 6.45(1H b),6.33(1H b),4.73(2H b),4.73(1H dd),4.50(1H t),4.28(1H d),3.86(2H q),3.61(1H dd),3.51(1H dd),3.24(3H s),3.21(3H s),2.89(1H d),2.83(1H d),1.98(3H s) |
| 26 | 4.68(1H dd),4.37(1H t),4.04(1H d),3.88(2H t),3.64(1H dd),3.55(1H dd),3.50(2H t),3.12(3H s),2.41(1H dd),2.39(1H d),2.30(3H s),1.95(3H s),(in CD₃OD) |
| 27 | 6.50(1H b),5.61(1H b),4.91(2H b),4.70(1H dd),4.48(1H t),4.27(1H d),3.79(2H q),3.59(1H dd),3.51(1H d),3.26(2H t),3.20(3H s),3.10(2H t),2.89(1H d),2.82(1H d),1.99(3H s),1.55(2H m),0.93(3H t) |
| 28 | 6.48(1H t),5.47(1H b),4.80(2H b),4.71(1H dd),4.49(1H t),4.27(1H d),3.78(2H q),3.60(1H dd),3.51(1H d),3.30(2H q),3.20(3H s),3.10(2H t),2.89(1H d),2.82(1H d),1.99(3H s),1.51(2H m),1.35(2H m),0.93(3H t) |

TABLE 4-continued

| No. | 'H—NMR (δ, CDCl₃, 270MHz) |
|---|---|
| 29 | 6.50(1H t),5.34(1H d),4.79(2H b), 4.71(1H dd),4.49(1H t),4.27(1H d), 3.78(3H q),3.60(1H dd),3.51(1H d), 3.20(3H s),3.09(2H t),2.89(1H d), 2.80(1H d),1.99(3H s),1.56-1.75 (6H m),1.27-1.43(2H m),1.09-1.23 (3H m) |
| 30 | 6.50(1H b),5.23(1H d),4.78(2H b), 4.71(1H dd),4.27(1H d),4.49(1H t), 3.90(1H t),3.78(2H t),3.60(1H dd), 3.51(1H d),3.20(3H s),3.10(2H t), 2.88(1H d),2.81(1H d),1.99(3H s), 1.49(1H m),1.16(3H d),0.91(3H t) |
| 31 | 4.70(2H b),4.64(1H dd),4.35(1H dd), 4.18(1H b),4.17(1H d),3.80(2H m), 3.55(4H m),3.21(3H s),3.05(2H m), 2.94(1H b),2.82(1H b),2.2-2.0 (4H m),1.97(3H s) |
| 32 | 6.49(1H b),4.72(2H b),4.71(1H dd), 4.53(1H dd),4.50(1H t),4.27(1H d), 3.75(3H s),3.58(1H dd),3.50(1H dd), 3.21(3H s),3.15(2H m),2.88(1H b), 2.81(1H b),2.3-2.0(4H m),1.98 (3H s) |
| 33 | 6.50(1H b),4.75(2H b),4.72(1H dd), 4.53(1H t),4.27(1H d),3.79(2H q), 3.70(4H m),3.60(1H dd),3.55(4H b), 3.21(3H s),3.14(2H t),2.90(1H d), 2.82(1H d),1.99(3H s) |
| 34 | 6.49(1H b),6.22(1H s),4.73(2H b), 4.70(1H dd),4.50(1H t),4.27(1H d), 3.77(2H q),3.60(1H dd),3.51(1H dd), 3.21(3H s),3.05(2H t),2.88(1H d), 2.81(1H d),1.98(3H s),1.56(6H s), 1.46(9H s) |
| 35 | 8.17(1H s),6.44(1H s),5.05(1H s), 4.73(1H dd),4.45-4.41(1H t),4.26 (1H d),3.79(2H q),3.58(1H dd),3.50 (2H m),3.25(3H s),3.21(3H s),3.09 (2H m),2.91(1H dd),2.84(1H d),1.97 (3H s) |
| 36 | 4.68(1H dd),4.37(1H t),4.04(1H d), 3.79(2H q),3.63(1H d),3.57(1H d), 3.18(3H s),3.08(2H m),2.49(1H dd), 2.41(1H d),2.30(3H s),1.95(3H s) (in CD₃OD) |
| 37 | 7.02(1H b),6.45(1H b),4.77(2H b), 4.72(1H dd),4.49(1H t),4.27(1H d), 3.86(2H q),3.60(1H dd),3.51(3H m), 3.21(3H s),2.89(1H d),2.82(1H d), 1.99(3H s),2.1-1.18(11H m) |
| 38 | 4.68(1H dd),4.37(1H t),4.37(1H b), 4.03(1H d),3.88(2H t),3.63(1H dd), 3.52(3H m),2.47(1H d),2.40(1H d), 2.30(3H s),1.94(3H s),2.00-1.38 (11H m)(in CD₃OD) |
| 39 | 7.30(1H b),6.42(1H b),4.85(2H b), 4.71(1H dd),4.47(1H t),4.27(1H d), 3.86(2H m),3.76(2H dd),3.60(1H dd), 3.51(3H m),3.21(3H s),2.89(1H d), 2.82(1H dd),1.99(3H s),1.26(3H t) |
| 40 | 7.18(1H b),6.40(1H b),4.75(2H b), 4.72(1H dd),4.49(1H t),3.86(2H q), 3.69(2H dd),3.60(1H dd),3.50(2H dd), 3.21(3H s),2.89(1H d),2.82(1H d), 1.73(2H m),0.98(3H t) |
| 41 | 7.31-7.12(5H m),6.53(1H b),4.71 (2H b),4.71(1H dd),4.53(1H t),4.27 (1H d),3.79(2H q),3.60(1H dd),3.51 (1H d),3.20(3H s),3.10(2H t),2.89 (1H d),2.81(1H d),2.55(2H d),1.99 (3H s),1.76-1.64(7H m),1.20(2H m) |
| 42 | 6.54(1H b),4.71(2H b),4.71(1H dd), 4.52(1H t),4.27(1H d),3.79(2H q), 3.60(1H dd),3.53(1H d),3.21(3H s), 3.11(2H t),2.89(1H d),2.81(1H d) 1.99(3H s),1.64-1.58(10H m) |
| 43 | 6.53(1H b),4.82(2H b),4.75(1H b), 4.45(1H t),4.27(1H d),3.79(2H b), 3.59(1H dd),3.51(2H dd),3.20(3H s), 3.15(2H b),2.90(1H d),2.28(1H d), |

TABLE 4-continued

| No. | 'H—NMR (δ, CDCl₃, 270MHz) |
|---|---|
| | 1.99(3H s),1.92(2H m),1.71(3H s), 1.55(2H m) |
| 44 | 6.31(1H b),4.93(2H b),4.68(2H b), 4.63(1H t),4.53(1H b),4.45(1H t), 4.27(1H d),3.81(2H m),3.75(3H s), 3.66(1H dd),3.60(2H dd),3.59(1H dd), 3.51(1H d),3.33(2H m),3.29(3H s), 2.90(1H b),2.83(1H b),2.15-2.0 (2H m),1.95(3H s) |
| 45 | 7.33(2H d),6.73(2H d),4.66(1H dd), 4.53(1H m),4.29(1H t),4.15(1H d), 3.79(2H q),3.5-3.6(2H m),3.55 (1H dd),3.48(1H dd),3.20(3H s),3.2- 3.1(2H m),2.97(1H d),2.86(1H d), 2.1-2.0(4H m),1.95(3H s) |
| 46 | 6.49(1H d),5.05(1H d),4.73(2H d), 4.70(1H dd),4.27(1H d),4.53(1H t), 3.79(2H q),3.60(1H dd),3.51(1H dd), 3.60(1H m),3.20(3H s),3.11(2H t), 2.88(1H d),2.82(1H b),1.99(3H s), 0.92(3H d),0.85(3H d) |
| 47 | 6.49(1H d),5.30(1H d),4.73(2H b), 4.72(1H d),4.52(1H t),4.27(1H d), 3.81(1H b),3.77(2H q),3.67(1H m), 3.60(1H dd),3.51(1H d),3.20(3H s), 3.11(2H t),2.88(1H b),1.99(3H s), 1.67-1.44(8H m),0.93(3H d),0.89 (3H d) |
| 48 | 6.53(1H b),5.91(1H d),5.02(2H bs), 4.68(1H dd),4.45(1H t),4.27(1H d), 3.85(1H m),3.71(3H m),3.57(2H d), 3.30(1H m),3.20(3H s),3.04(2H m), 1.82(1H bs),0.95(6H t) |
| 49 | 8.53(1H d),7.65(1H t),7.19(2H d), 6.68(1H b),6.50(1H b),4.82(2H b), 4.70(1H dd),4.49(1H t),4.27(1H d), 3.77(2H q),3.75(2H q),3.59(1H dd), 3.51(1H dd),3.20(3H s),3.09(3H t), 3.03(3H t),2.89(1H d),2.80(1H d), 1.98(3H s) |
| 50 | 7.61(1H d),7.39-7.22(10H m),6.85 (1H d),6.49(1H b),4.73(2H b),4.70 (1H dd),4.49(1H t),4.26(1H d),3.86 (2H q),3.59(1H dd),3.51(2H t),3.19 (3H s),2.88(1H d),2.81(1H d),1.97 (3H s) |

TABLE 5

| No. | MS | IR (KBr; cm⁻¹) | | | |
|---|---|---|---|---|---|
| 1 | 453(M + 2) | 3270 1330 | 1705 1225 | 1640 | 1570 | 1550 |
| 2 | 597(") | 3400 1517 | 2950 1445 | 1715 1330 | 1655 1260 | 1550 |
| 3 | 601(") | 3100 1330 | 1720 1060 | 1640 | 1550 | 1515 |
| 4 | 495(") | 3450 1330 | 2950 1060 | 1710 | 1550 | 1517 |
| 5 | 495(") | 3400 | 1710 | 1640 | 1550 | 1330 |
| 6 | 551(") | 3400 1330 | 2950 1060 | 1720 | 1638 | 1550 |
| 7 | 481(") | 3400 1561 1062 | 3270 1523 | 2972 1450 | 1715 1324 | 1654 1215 |
| 8 | 467(") | 3290 1511 | 2930 1446 | 1718 1329 | 1632 1097 | 1555 1063 |
| 9 | 553(") | 3400 1510 | 2950 1330 | 1705 1060 | 1635 | 1550 |
| 10 | 677(") | 3400 1450 | 1720 1115 | 1640 1205 | 1550 1060 | 1510 |
| 11 | 509(") | 3450 1645 1210 | 3300 1557 1065 | 2960 1513 | 2935 1450 | 1717 1329 |
| 12 | 612(") | 3330 1550 1060 | 3280 1515 | 2925 1450 | 1710 1330 | 1640 1210 |
| 13 | 615(") | 3270 1507 | 2960 1452 | 1715 1328 | 1635 1209 | 1656 1063 |
| 14 | 624(") | 3450 | 3280 | 2930 | 1715 | 1635 |

TABLE 5-continued

| No. | MS | IR (KBr; cm$^{-1}$) | | | | |
|---|---|---|---|---|---|---|
| | | 1550 | 1517 | 1450 | 1322 | 1220 |
| | | 1064 | | | | |
| 15 | 592(M + 2) | 3450 | 3300 | 2975 | 2925 | 1723 |
| | | 1640 | 1557 | 1515 | 1450 | 1365 |
| | | 1322 | 1220 | 1150 | 1060 | |
| 16 | 627(") | 3450 | 3300 | 2950 | 1719 | 1653 |
| | | 1557 | 1515 | 1451 | 1372 | 1326 |
| | | 1167 | 1063 | | | |
| 17 | 550(") | 3400 | 3300 | 2950 | 1715 | 1636 |
| | | 1554 | 1508 | 1451 | 1412 | 1330 |
| | | 1219 | 1064 | | | |
| 18 | 564(") | 3430 | 3290 | 2930 | 1716 | 1635 |
| | | 1508 | 1451 | 1373 | 1328 | 1217 |
| | | 1139 | 1001 | 757 | | |
| 19 | 536(") | 3425 | 3300 | 2950 | 1682 | 1636 |
| | | 1557 | 1517 | 1458 | 1329 | 968 |
| 20 | 651(") | 3450 | 3300 | 2975 | 1715 | 1652 |
| | | 1558 | 1515 | 1455 | 1327 | 1111 |
| | | 1062 | 987 | | | |
| 21 | 492(") | 3450 | 3300 | 2950 | 1715 | 1635 |
| | | 1556 | 1509 | 1450 | 1378 | 1327 |
| | | 1222 | 1062 | | | |
| 22 | 529(") | 3280 | 3028 | 2930 | 2854 | 1713 |
| | | 1637 | 1557 | 1505 | 1451 | 1328 |
| | | 1215 | 1109 | 1063 | 700 | |
| 23 | 467(") | 3450 | 3278 | 2970 | 2934 | 1714 |
| | | 1635 | 1606 | 1549 | 1507 | 1450 |
| | | 1413 | 1326 | 1217 | 1064 | 854 |
| | | 758 | | | | |
| 24 | 495(") | 3450 | 3290 | 2958 | 1715 | 1662 |
| | | 1635 | 1605 | 1556 | 1511 | 1453 |
| | | 1329 | 1214 | 1111 | 1064 | |
| 25 | 469(") | 3450 | 3300 | 1708 | 1634 | 1600 |
| | | 1543 | 1506 | 1448 | 1330 | 1221 |
| | | 1064 | | | | |
| 26 | 469(M + 2) | 3300 | 2950 | 1714 | 1634 | 1543 |
| | | 1505 | 1447 | 1332 | 1159 | 1109 |
| | | 1050 | | | | |
| 27 | 481(") | 3450 | 3284 | 2962 | 2934 | 2876 |
| | | 1714 | 1660 | 1634 | 1557 | 1504 |
| | | 1450 | 1328 | 1213 | 1111 | 1063 |
| 28 | 495(") | 3450 | 3288 | 2956 | 2932 | 1716 |
| | | 1634 | 1557 | 1507 | 1450 | 1416 |
| | | 1328 | 1214 | 1113 | 1064 | |
| 29 | 521(") | 3450 | 3290 | 2932 | 2854 | 1716 |
| | | 1635 | 1553 | 1508 | 1449 | 1328 |
| | | 1210 | 1064 | 758 | | |
| 30 | 495(") | 3450 | 3300 | 2960 | 2932 | 1715 |
| | | 1635 | 1555 | 1506 | 1450 | 1414 |
| | | 1328 | 1214 | 1166 | 1063 | |
| 31 | 557(") | 3450 | 3300 | 2948 | 1716 | 1638 |
| | | 1542 | 1506 | 1451 | 1374 | 1330 |
| | | 1190 | 1065 | | | |
| 32 | 551(") | 3450 | 3300 | 2952 | 1725 | 1652 |
| | | 1558 | 1517 | 1452 | 1327 | 1216 |
| | | 1063 | | | | |
| 33 | 509(") | 3450 | 3300 | 2924 | 1717 | 1638 |
| | | 1556 | 1508 | 1449 | 1410 | 1328 |
| | | 1214 | 1065 | 1020 | | |
| 34 | 581(") | 3450 | 3300 | 2980 | 2934 | 1707 |
| | | 1635 | 1543 | 1505 | 1450 | 1329 |
| | | 1225 | 1146 | 1064 | | |
| 35 | 496(") | 3450 | 3284 | 2936 | 1695 | 1634 |
| | | 1555 | 1512 | 1454 | 1411 | 1329 |
| | | 1276 | 1222 | 1065 | | |
| 36 | 496(") | 3450 | 3262 | 2950 | 1696 | 1634 |
| | | 1555 | 1514 | 1455 | 1418 | 1338 |
| | | 1278 | 1157 | 1114 | 1062 | |
| 37 | 537(M + 2) | 3450 | 3280 | 2930 | 1706 | 1635 |
| | | 1557 | 1507 | 1448 | 1328 | 1063 |
| 38 | 537(") | 3450 | 3280 | 2930 | 1708 | 1634 |
| | | 1541 | 1516 | 1335 | 1155 | 1111 |
| | | 1059 | 984 | | | |
| 39 | 483(") | 3450 | 3280 | 2930 | 1720 | 1635 |
| | | 1554 | 1510 | 1450 | 1327 | 1064 |
| 40 | 497(") | 3450 | 3290 | 2964 | 1710 | 1635 |
| | | 1554 | 1507 | 1450 | 1328 | 1063 |
| 41 | 597(") | 3450 | 3295 | 2925 | 1716 | 1634 |
| | | 1556 | 1507 | 1448 | 1416 | 1328 |
| | | 1219 | 1062 | | | |
| 42 | 507(") | 3450 | 3280 | 2945 | 1716 | 1636 |
| | | 1558 | 1504 | 1446 | 1414 | 1322 |
| | | 1211 | 1061 | | | |
| 43 | 523(") | 3440 | 3280 | 2934 | 1708 | 1635 |
| | | 1561 | 1543 | 1449 | 1417 | 1327 |
| | | 1195 | 1066 | | | |
| 44 | 567(") | 3450 | 1716 | 1637 | 1562 | 1554 |
| | | 1516 | 1452 | 1329 | 1215 | 1065 |
| 45 | 628(") | 3256 | 1707 | 1634 | 1541 | 1516 |
| | | 1448 | 1327 | 1219 | 1062 | |
| 46 | 537(") | 3294 | 2962 | 1713 | 1636 | 1552 |
| | | 1509 | 1450 | 1330 | 1062 | |
| 47 | 549(") | 3288 | 2928 | 1710 | 1635 | 1547 |
| | | 1511 | 1445 | 1326 | 1205 | 1062 |
| 48 | 525(") | 3440 | 3278 | 2962 | 1713 | 1633 |
| | | 1553 | 1513 | 1451 | 1415 | 1329 |
| | | 1207 | 1111 | 1064 | | |
| 49 | 544(") | 3440 | 3284 | 2928 | 1715 | 1634 |
| | | 1552 | 1509 | 1450 | 1329 | 1214 |
| | | 1110 | 1063 | | | |
| 50 | 621(") | 3450 | 3190 | 1715 | 1634 | 1602 |
| | | 1554 | 1508 | 1448 | 1329 | 1217 |
| | | 1062 | | | | |

The pharmacological activities of selected Compounds (I) are shown by way of the following experiments.

Experiment 1

The effects of selected Compounds (I) against Sarcoma 180 solid tumour are shown in the following Table 6. In this table, the term (CI)c denotes (CI of the test compound)/(CI of mitomycin C), and the term (WBC$_{4000}$/(ED$_{50}$)c denotes [(WBC$_{4000}$/(ED$_{50}$) of the test compound]/[(WBC$_{4000}$/(ED$_{50}$) of mitomycin C].

TABLE 6

| No. | LD$_{50}$(mg/kg) | ED$_{50}$(mg/kg) | (CI)$_c$ | (WBC$_{4000}$ ED$_{50}$)$_c$ |
|---|---|---|---|---|
| *1 | >100 | 25.8 | >1.39 | 1.16 |
| *2 | 45 | 11.2 | 1.44 | 2.53 |
| 3 | >100 | 39.6 | >0.89 | >2.11 |
| 4 | 45 | 13.3 | 1.64 | 0.81 |
| *5 | 30 | 8.8 | 1.22 | 1.06 |
| *6 | >50 | 10.1 | 1.77 | 2.39 |
| *7 | 45 | 7.0 | 2.29 | 1.69 |
| 8 | 26.3 | 14.4 | 0.65 | 1.80 |
| 9 | 37.5 | 15.9 | 0.81 | >0.89 |
| 10 | >100 | 95.5. | >0.43 | >1.08 |
| 11 | 45 | 11.1 | 1.40 | 0.89 |
| *12 | 37.5 | 8.1 | 1.61 | 3.41 |
| *13 | 26.3 | 4.5 | 2.01 | 2.20 |
| *14 | 75 | 13.6 | 2.23 | 1.94 |
| 16 | >100 | 84.4 | >0.45 | >1.40 |
| *17 | 75 | 21.7 | 1.32 | 1.04 |
| *18 | 97.5 | 12.3 | 3.02 | 1.85 |
| *19 | 75 | 19.6 | 1.46 | 1.50 |
| *21 | 37.5 | 8.4 | 1.44 | 1.87 |
| *22 | 37.5 | 10.2 | 1.44 | 2.35 |
| *23 | 52.5 | 8.3 | 2.48 | 2.25 |
| 24 | 22.5 | 9.9 | 0.89 | 1.64 |
| *25 | 52.5 | 10.5 | 1.96 | 2.55 |
| *27 | 37.5 | 11.1 | 1.33 | 1.75 |
| *28 | 43.8 | 9.9 | 1.73 | 1.12 |
| 29 | 43.8 | 12.0 | 1.43 | 0.89 |
| 30 | 37.5 | 9.6 | 1.53 | 0.82 |
| 32 | 67.5 | 17.9 | 1.48 | 0.89 |
| *33 | 52.5 | 17.8 | 1.23 | 1.06 |
| *34 | 37.5 | 13.7 | 1.14 | 1.06 |
| 35 | 105 | 27.9 | 1.30 | 0.51 |
| 37 | 41.3 | 23.5 | 0.73 | 0.56 |
| 38 | 75 | 39.5 | 0.79 | 1.38 |
| *39 | 45 | 7.8 | 2.40 | 2.06 |
| *40 | >25 | 10.1 | >1.03 | 1.57 |
| *41 | 41.3 | 13.67 | 1.37 | 1.37 |

TABLE 6-continued

| No. | LD$_{50}$(mg/kg) | ED$_{50}$(mg/kg) | (CI)$_c$ | (WBC$_{4000}$ ED$_{50}$)$_c$ |
| --- | --- | --- | --- | --- |
| *42 | 33.8 | 9.34 | 1.14 | 1.46 |
| *43 | 52.5 | 9.15 | 2.17 | 1.81 |
| *44 | >100 | 27.5 | >1.85 | 1.47 |
| 45 | >100 | 89.1 | >0.51 | 1.00 |
| *46 | 37.5 | 12.5 | 1.27 | 2.83 |
| *48 | 45 | 14.3 | 1.39 | 1.07 |
| *49 | 75 | 22.8 | 1.57 | 2.14 |

This table indicates that the compounds marked with * exhibit higher C.I. vales and higher WBC$_{4000}$ values ED$_{50}$ than the corresponding values of mitomycin C.

LD$_{50}$, ED$_{50}$ and WBC$_{4000}$ were respectively determined as follows:

(1) LD$_{50}$

Each animal of the test group, consisting of 5 ddy mice, was administered once with a test compound by abdominal injection. After this, the animals were observed for 14 days to note the survival ratio. To determine the LD$_{50}$ value, Behrens-Koerber's method was applied.

(2) ED$_{50}$ $5 \times 10^6$ sarcoma 180 solid tumor cells were abdominally implanted into ddy mice. 7 days after this, ascites cells were sampled. The cells were washed once with a sterilized physiological saline and were used to prepare a cell suspension containing $5 \times 10^7$ cells per ml of a sterilized physiological saline. On each occasion, 0.1 ml of the cell suspension was subcutaneously implanted under the skin of the right armpit of a male mouse (ddy strain; body weight $20 \pm 2$ g). The test compound which was dissolved in a physiological saline with or without addition of Tween 80 was injected into the tail vein of each animal of a group consisting of 5 mice at a dose of 0.1–0.2 ml 24 hours after the implantation of the tumor cells.

The anti-tumor activity was determined in the following manner:

7 days after the implantation, the major axis (a) and the minor axis (b) of the tumour were measured to calculate a value of $(a \times b^2)/2$ which corresponds to the volume of the tumour. The antitumour activity was expressed by the ratio of the volume of the tumour (T) of the group of animals administered with the test compound to the corresponding volume of tumours (C) of the untreated animals.

On graph paper, T/C was plotted on the ordinate using an arithmetic scale and the administered amount of test compound was plotted on the abscissa using a logarithmic scale. The relationship between the dose and T/C was shown by a straight line determined by the method of least squares, from which ED$_{50}$ viz. a dose corresponding to T/C of 0.5 was obtained.

(3) WBC$_{4000}$ $5 \times 10^6$ Sarcoma 180 solid tumor cells were subcutaneously implanted into the right armpit of each mouse (body weight of $20 \pm 2$ g) of a group consisting of 5 male mice (ddy strain). 24 hours after implantation, a test compound was administered (i.p.) to each mouse. 4 days later, blood (0.02 ml) was collected from the suborbital plexus vein of each tumour-carrying mouse. The collected sample of blood was dispersed dropwise in 9.98 ml of Cell-kit Seven solution. One drop of saponin solution was added to the sample to dissolve erythrocytes and then a microcell-counter was used to measure the number of leucocytes. On graph paper, the number of leucocytes was indicated on the y-axis using an arithmetic scale and the dose of the test compound was indicated on the x-axis using a logarithmic scale. The relationship between the number of peripheral leucocytes and the dosage of the drug was plotted and WBC$_{4000}$ viz. the dosage corresponding to 4000 peripheral leucocytes per mm$^3$ (about half of the number of leucocytes of normal mice) was obtained.

Experiment 2

The experiment was carried out in the following manner. $1 \times 10^6$ lymphocytic Leukemia P-388 tumour cells were abdominally implanted into each mouse of a group consisting of 5 mice (body weight about 22 g; female of CDF strain). 24 hours after implantation, a physiological saline solution (0.2 ml) containing the test compound with or without addition of Tween 80 was abdominally given to the test animal. The death ratio of the animals was observed for 30 days.

Table 7 indicates anti-tumour activities of selected Compounds (I) against lyphocytic Leukemia P-388.

TABLE 7

| Compound No. | OPD(mg/kg) | Dose (mg/kg)* | (ILS$_{max}$)$_c$ | (TI)$_c$ |
| --- | --- | --- | --- | --- |
| 1 | 25 | 0.78 | 1.44 | 1.33 |
| 4 | 25 | 2.02 | >1.21 | 1.18 |
| 5 | 25 | 1.32 | >1.17 | 1.80 |
| 6 | 100 | 1.10 | >1.82 | 9.09 |
| 7 | 12.5 | 0.77 | >1.76 | 2.48 |
| 9 | 12.5 | 0.84 | >1.54 | 0.92 |
| 11 | 25 | 1.04 | >1.47 | 1.86 |
| 12 | 12.5 | <0.78 | >1.47 | >1.10 |
| 13 | 7.5 | 0.33 | >2.57 | 1.96 |
| 14 | 50 | 3.46 | 1.44 | 0.93 |
| 22 | 25 | 0.62 | 1.43 | 3.36 |
| 23 | 25. 12.5 | 0.33 | 1.16 | 3.28~1.64 |
| 24 | 25 | 0.50 | 1.26 | 2.16 |
| 27 | 25 | 0.67 | 1.84 | 3.11 |
| 29 | 25 | 0.85 | 1.69 | 2.45 |
| 30 | 25 | 0.65 | 1.60 | 3.20 |
| 32 | 37.5 | 1.67 | 1.40 | 2.14 |
| 39 | 25 | 0.57 | >1.60 | 2.74 |
| 50 | 12.5 | 0.74 | >2.39 | 1.10 |

Notes:
* = Dose needed to give ILS$_{30}$.
(ILS$_{max}$)$_c$ = (ILS$_{max}$ of test compound)/(ILS$_{max}$ of mitomycin C)
(TI)$_c$ = (TI of test compound)/(TI of mitomycin C)

We claim:
1. Mitomycin compounds represented by the formula:

$$\underset{A-C(OCH_2)_nS(CH_2)_mNH}{\overset{X}{\|}} \text{—[mitomycin core with } CH_2OCNH_2, OR_1, NR_b\text{]} \quad (I)$$

wherein
A is selected from the following (i) to (v):

$$\underset{R_2}{\overset{R_1}{>}}N- \quad (i)$$

wherein $R_1$ is selected from the group consisting of unsubstituted or substituted $C_1$ to $C_{18}$ alkyl (wherein the substituent is one or more members independently selected from lower alkoxycarbonyl, benzyloxy, benzyloxycarbonyl, carboxy, halogen, hydroxy, lower alkoxy, lower alkanoyloxy, trilower alkylsilyloxy, amino, lower alkylamino, dilower alkylamino and benzyloxycarbonylamino), unsubstituted or substituted $C_3$ to $C_6$ cycloalkyl (wherein the substituent is one or more members independently selected from lower alkyl, lower alkoxycarbonyl, benzyloxycarbonyl, carboxy, halogen, hydroxy, lower alkoxy, lower alkanoyloxy, trilower alkylsilyloxy, amino, lower alkylamino, dilower alkylamino and benzyloxycarbonyl-amino unsubstituted or substituted aralkyl selected from the group consisting of benzyl, phenethyl and diphenylmethyl wherein the benzene nucleus is substituted by one or more members independently selected from lower alkoxy, halogen, lower alkyl, nitro, hydroxy, amino, cyano and carboxy), 2-benzyloxycarbonyl-1-phenylethyl and

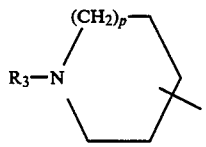

(wherein $R_3$ is selected from the group consisting of hydrogen, benzyl, lower alkyl, lower alkanoyl and benzyloxycarbonyl; and p is 0 or 1) and $R_2$ represents hydrogen; or $R_1$ and $R_2$ each independently represents $C_1$ to $C_{18}$ alkyl;

(ii) morpholino;

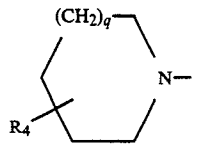  (iii)

wherein $R_4$ is selected from the group consisting of hydrogen, hydroxy, lower alkoxy, lower alkanoyloxy, lower alkylamino, dilower alkylamino, benzyloxycarbonylamino and benzyl; and q is 0 or 1;

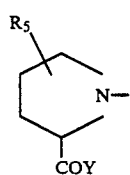  (iv)

wherein $R_5$ represents hydrogen or hydroxy; Y is selected from the group consisting of hydroxy, lower alkoxy, benzyloxy, lower alkanoyloxymethoxy, amino, lower alkylamino, dilower alkylamino, benzylamino or

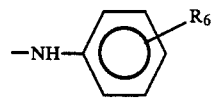

(wherein $R_6$ represents hydrogen or hydroxy); and

  (v)

wherein $R_7$ is selected from the group consisting of hydrogen, lower alkanoyl, trifluoroacetyl, benzoyl, benzyloxycarbonyl, lower alkoxycarbonyl, lower alkyl and benzyl; and $R_8$ represents hydrogen or lower alkyl;

n is 0 or 1, provided that when n is 0, X represents oxygen or sulphur and when n is 1, X is oxygen;

m is an integer of from 2 to 8; and $R_a$ and $R_b$ each independently represents hydrogen or methyl provided that $R_a$ and $R_b$ do not both represent hydrogen, and carboxylic acid salts thereof.

2. Mitomycin compounds according to claim 1 wherein A represents

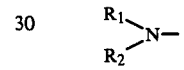

wherein $R_1$ is selected from the group consisting of methyl, ethyl, propyl, isopropyl, n-butyl, isobutyl, sec-butyl, tert-butyl, n-pentyl, isopentyl, tert-pentyl, neopentyl, n-hexyl, isohexyl, 3-methylpentyl, 2-methylpentyl, 1-methylpentyl, 1,3-dimethylbutyl, 3,3-dimethylbutyl, 2-ethylbutyl, 2,4-dimethyl-3-pentyl, 2,2-dimethyl-3-pentyl, 2,2-dimethyl-3-pentyl, n-octyl, 2-ethylhexyl, 2,2,4,4-tetramethyl-3-pentyl, n-decyl and n-octadecyl, unsubstituted or substituted with one or more substituents independently selected from straight or branched alkoxycarbonyl carrying 2–5 carbon atoms, fluorine, chlorine and bromine; and $R_2$ represents hydrogen or a group as defined herein for $R_1$.

3. Mitomycin compounds according to claim 1, wherein

X is oxygen or sulphur;

n is 0;

m is an integer of from 2 to 8;

$R_a$ is methyl;

$R_b$ is hydrogen;

lected from the following (i)–(iv):

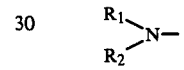  (i)

wherein $R_1$ is selected from the group consisting of unsubstituted $C_1$ to $C_{18}$ alkyl, benzyloxy-substituted $C_1$ to $C_{18}$ alkyl, unsubstituted aralkyl selected from the group consisting of benzyl, phenethyl and diphenylmethyl, and

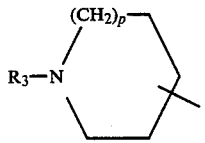

(wherein $R_3$ is benzyl; p is 0 or 1) and $R_2$ represents hydrogen;

(ii) morpholino;

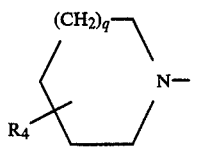

wherein $R_4$ represents hydrogen, hydroxy and benzyl; and q is 0 or 1;

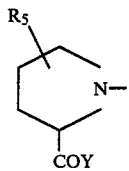

wherein $R_5$ represents hydrogen or hydroxy, and Y is selected from the group consisting of lower alkoxy, amino, lower alkylamino, dilower alkylamino, and benzylamino.

4. Mitomycin compounds according to claim 1 wherein
A represents $R_1$
  \N—
$R_2$ (wherein $R_1$ is unsubstituted benzyl);
m is 2;
9  10 represents ━ ; and
X, n, Ra, Rb, and $R_2$ are as defined in claim 3.

5. Mitomycin compounds according to claim 1 selected from the group consisting of:
7-N-(2-methylaminocarbonylthioethyl)mitomycin C;
7-N-[2-(2-t-butoxycarbonylethyl)aminocarbonyloxymethylthioethyl]mitomycin C;
7-N-(2-t-butylaminocarbonylthioethyl)mitomicin C;
7-N-]2-((S)-2-methoxycarbonylpyrrolidino)carbonylthioethyl]mitomycin C;
7-N-(2-isopropylaminocarbonylthioethyl)mitomycin C;
7-N-[2-(1-benzyl-piperidine-4-yl)aminocarbonylthioethyl]mitomycin C;
7-N-[(2-(1-benzyloxymethyl-2-methylpropyl)aminocarboonylthioethyl)]mitomycin C;
7-N-[2-((S)-2-benzylaminocarbonylpyrrolidino)carbonylthioethyl]mitomycin C;
7-N-[2-((S)-2-methylaminocarbonylpyrrolidino)carbonylthioethyl]mitomycin C;
7-N-[2-((S)-2-dimethylaminocarbonylpyrrolidino)carbonylthioethyl]mitomycin C;
7-N-[2-((S)-2-carbamoylpyrrolidino)carbonylthioethyl]mitomycin C;
7-N-(2-pyrrolidinocarbonylthioethyl)mitomycin C;
7-N-(2-benzylaminocarbonylthioethyl)mitomycin C;
7-N-(2-ethylaminocarbonylthioethyl)mitomycin C;
7-N-(2-methylaminothiocarbonylthioethyl)mitomycin C;
7-N-(2-n-propylaminocarbonylthioethyl)mitomycin C;
7-N-(2-butylaminocarbonylthioethyl)mitomycin C;
7-N-(2-morpholinocarbonylthioethyl]mitomycin C;
7-N-[2-(1-methyl-1-t-butoxycarbonylethyl)aminocarbonylthioethyl]mitomycin C;
7-N-(2-ethylaminothiocarbonylthioethyl)mitomycin C;
7-N-(2-n-propylaminothiocarbonylthioethyl)mitomycin C;
7-N-[2-(4-benzylpiperidino)carbonylthioethyl]mitomycin C;
7-N-(2-piperidinocarbonylthioethyl)mitomycin C;
7-N-[2-(4-hydroxypiperidino)carbonylthioethyl]mitomycin C;
7-N-[2-((S)-2-methoxycarbonyl-(SR)-4-hydroxypyrrolidino)carbonylthioethyl]mitomycin C;
7-N-[2-(1-isopropyl-2-methylpropyl)aminocarbonylthioethyl]mitomycin C;
7-N-[2-(1-hydroxymethyl-2-methylpropyl)aminocarbonylthioethyl]mitomycin C; and
7-N-[2-{2-(2-pyridyl)ethyl}aminocarbonylthioethyl]mitomycin C.

6. A pharmaceutical having antitumour activity comprising a pharmacologically effective amount of a mitomycin compound according to claim 1 in association with at least one pharmaceutically acceptable carrier or adjuvant.

7. A pharmaceutical composition having antitumor activity against solid Sarcoma 180 tumors and lymphocytic Leukemia P-388 tumors comprising a pharmacologically effective amount of a mitomycin derivative of claim 5 in association with a pharmaceutically acceptable carrier or adjuvant.

8. The pharmaceutical composition having antitumor activity of claim 6 containing a sufficient amount of mitomycin derivative to be effective as an anti-tumour agent when administered to a mammal.

9. A method for combatting tumors in an animal subject which comprises administering the pharmaceutical composition of claim 6 to a mammal at a daily dosage in the range of 0.5 to 75 mg/kg of body weight.

* * * * *